(12) United States Patent
Levin et al.

(10) Patent No.: US 8,317,808 B2
(45) Date of Patent: Nov. 27, 2012

(54) DEVICE AND METHOD FOR ROLLING AND INSERTING A PROSTHETIC PATCH INTO A BODY CAVITY

(75) Inventors: Ofek Levin, Moshav Amirim (IL); Arie Levy, Ramat-Gan (IL)

(73) Assignee: Covidien LP, Mansfield, MA (US)

( * ) Notice: Subject to any disclaimer, the term of this patent is extended or adjusted under 35 U.S.C. 154(b) by 85 days.

(21) Appl. No.: 12/889,774

(22) Filed: Sep. 24, 2010

(65) Prior Publication Data

US 2011/0034942 A1 Feb. 10, 2011

Related U.S. Application Data

(63) Continuation-in-part of application No. 12/834,456, filed on Jul. 12, 2010, which is a continuation-in-part of application No. PCT/IL2009/000188, filed on Feb. 18, 2009.

(60) Provisional application No. 61/029,386, filed on Feb. 18, 2008, provisional application No. 61/300,455, filed on Feb. 2, 2010.

(51) Int. Cl.
*A61B 17/08* (2006.01)
*A61F 2/02* (2006.01)

(52) U.S. Cl. ...................... 606/151; 623/23.72

(58) Field of Classification Search .............. 623/1.11, 623/23.72; 606/99, 151, 198; 600/29, 30, 600/37; 206/363, 438, 440, 441
See application file for complete search history.

(56) References Cited

U.S. PATENT DOCUMENTS

| | | | |
|---|---|---|---|
| 4,347,847 A | 9/1982 | Usher |
| 4,400,833 A | 8/1983 | Kurland |
| 4,452,245 A | 6/1984 | Usher |
| 4,485,816 A | 12/1984 | Krumme |
| 4,585,458 A | 4/1986 | Kurland |
| 4,633,873 A | 1/1987 | Dumican et al. |
| 4,838,884 A | 6/1989 | Dumican et al. |
| 4,854,316 A | 8/1989 | Davis |
| 5,019,096 A | 5/1991 | Fox, Jr. et al. |
| 5,116,357 A | 5/1992 | Eberbach |
| 5,122,155 A | 6/1992 | Eberbach |
| 5,125,553 A | 6/1992 | Oddsen et al. |
| 5,141,515 A | 8/1992 | Eberbach |
| 5,147,374 A | 9/1992 | Fernandez |
| 5,176,692 A | 1/1993 | Wilk et al. |
| 5,203,864 A | 4/1993 | Phillips |
| 5,219,077 A | 6/1993 | Transue |
| 5,249,682 A | 10/1993 | Transue |
| 5,254,133 A | 10/1993 | Seid |
| 5,258,000 A | 11/1993 | Gianturco |
| 5,263,969 A | 11/1993 | Phillips |

(Continued)

FOREIGN PATENT DOCUMENTS

CA 2413904 A1 10/2003

(Continued)

OTHER PUBLICATIONS

US 6,503,260, 01/2003, Schaller et al. (withdrawn)

*Primary Examiner* — Julian Woo

(57) ABSTRACT

This invention generally relates to minimal invasive surgery. More specifically the current invention relates to an apparatus especially adapted to fold prosthetic patches and to insert said patches into a body cavity through a cannula or an incision.

16 Claims, 16 Drawing Sheets

U.S. PATENT DOCUMENTS

| | | |
|---|---|---|
| 5,289,963 A | 3/1994 | McGarry et al. |
| 5,290,217 A | 3/1994 | Campos |
| 5,292,328 A | 3/1994 | Hain et al. |
| 5,304,187 A | 4/1994 | Green et al. |
| 5,333,624 A | 8/1994 | Tovey |
| 5,354,292 A | 10/1994 | Braeuer et al. |
| 5,356,064 A | 10/1994 | Green et al. |
| 5,356,432 A | 10/1994 | Rutkow et al. |
| 5,364,002 A | 11/1994 | Green et al. |
| 5,364,004 A | 11/1994 | Davidson |
| 5,366,460 A | 11/1994 | Eberbach |
| 5,368,602 A | 11/1994 | de la Torre |
| 5,370,650 A | 12/1994 | Tovey et al. |
| 5,376,097 A | 12/1994 | Phillips |
| 5,383,477 A | 1/1995 | DeMatteis |
| 5,392,978 A | 2/1995 | Velez et al. |
| 5,397,331 A | 3/1995 | Himpens et al. |
| 5,405,360 A | 4/1995 | Tovey |
| 5,425,357 A | 6/1995 | Moll et al. |
| 5,425,740 A | 6/1995 | Hutchinson |
| 5,433,996 A | 7/1995 | Kranzler et al. |
| 5,464,403 A | 11/1995 | Kieturakis et al. |
| 5,497,933 A | 3/1996 | Defonzo et al. |
| 5,531,759 A | 7/1996 | Kensey et al. |
| 5,560,224 A | 10/1996 | Tessler |
| 5,560,532 A | 10/1996 | DeFonzo et al. |
| 5,564,615 A | 10/1996 | Bishop et al. |
| 5,569,273 A | 10/1996 | Titone et al. |
| 5,577,654 A | 11/1996 | Bishop |
| 5,588,580 A | 12/1996 | Paul et al. |
| 5,588,581 A | 12/1996 | Conlon et al. |
| 5,601,224 A | 2/1997 | Bishop et al. |
| 5,614,284 A | 3/1997 | Kranzler et al. |
| 5,618,290 A | 4/1997 | Toy et al. |
| 5,626,587 A | 5/1997 | Bishop et al. |
| 5,634,584 A | 6/1997 | Okorocha et al. |
| 5,634,931 A | 6/1997 | Kugel |
| 5,662,662 A | 9/1997 | Bishop et al. |
| 5,695,525 A | 12/1997 | Mulhauser et al. |
| 5,716,409 A | 2/1998 | Debbas |
| 5,725,577 A | 3/1998 | Saxon |
| 5,728,119 A | 3/1998 | Smith et al. |
| 5,749,895 A | 5/1998 | Sawyer et al. |
| 5,766,246 A | 6/1998 | Mulhauser et al. |
| 5,769,864 A | 6/1998 | Kugel |
| 5,779,728 A | 7/1998 | Lunsford et al. |
| 5,810,851 A | 9/1998 | Yoon |
| 5,814,058 A | 9/1998 | Carlson et al. |
| 5,817,109 A | 10/1998 | McGarry et al. |
| 5,824,082 A | 10/1998 | Brown |
| 5,836,961 A | 11/1998 | Kieturakis et al. |
| 5,854,383 A | 12/1998 | Erneta et al. |
| 5,863,531 A | 1/1999 | Naughton et al. |
| 5,865,728 A | 2/1999 | Moll et al. |
| 5,911,726 A | 6/1999 | Belknap |
| 5,916,225 A | 6/1999 | Kugel |
| 5,925,058 A | 7/1999 | Smith et al. |
| 5,951,997 A | 9/1999 | Bezwada et al. |
| 5,954,767 A | 9/1999 | Pajotin et al. |
| 5,972,007 A | 10/1999 | Sheffield et al. |
| 5,972,008 A | 10/1999 | Kalinski et al. |
| 5,990,378 A | 11/1999 | Ellis |
| 6,004,333 A | 12/1999 | Sheffield et al. |
| 6,042,592 A | 3/2000 | Schmitt |
| 6,066,776 A | 5/2000 | Goodwin et al. |
| 6,066,777 A | 5/2000 | Benchetrit |
| 6,090,116 A | 7/2000 | D'Aversa et al. |
| 6,113,609 A | 9/2000 | Adams |
| 6,113,611 A | 9/2000 | Allen et al. |
| 6,113,624 A | 9/2000 | Bezwada et al. |
| 6,166,286 A | 12/2000 | Trabucco |
| 6,171,318 B1 | 1/2001 | Kugel et al. |
| 6,174,320 B1 | 1/2001 | Kugel et al. |
| 6,176,863 B1 | 1/2001 | Kugel et al. |
| 6,197,036 B1 | 3/2001 | Tripp et al. |
| 6,214,020 B1 | 4/2001 | Mulhauser et al. |
| 6,224,616 B1 | 5/2001 | Kugel |
| 6,241,768 B1 | 6/2001 | Agarwal et al. |
| 6,258,113 B1 | 7/2001 | Adams et al. |
| 6,258,124 B1 | 7/2001 | Darois et al. |
| 6,267,772 B1 | 7/2001 | Mulhauser et al. |
| 6,280,453 B1 | 8/2001 | Kugel et al. |
| 6,287,316 B1 | 9/2001 | Agarwal et al. |
| 6,290,708 B1 | 9/2001 | Kugel et al. |
| 6,312,442 B1 | 11/2001 | Kieturakis et al. |
| 6,319,264 B1 | 11/2001 | Tormala et al. |
| 6,368,541 B1 | 4/2002 | Pajotin et al. |
| 6,375,662 B1 | 4/2002 | Schmitt |
| 6,383,201 B1 | 5/2002 | Dong |
| 6,391,060 B1 | 5/2002 | Ory et al. |
| 6,408,656 B1 | 6/2002 | Ory et al. |
| 6,416,486 B1 | 7/2002 | Wampler |
| 6,425,900 B1 | 7/2002 | Knodel et al. |
| 6,425,924 B1 | 7/2002 | Rosseau |
| 6,436,030 B2 | 8/2002 | Rehil |
| 6,447,524 B1 | 9/2002 | Knodel et al. |
| 6,478,803 B1 | 11/2002 | Kapec et al. |
| 6,485,503 B2 | 11/2002 | Jacobs et al. |
| 6,497,650 B1 | 12/2002 | Nicolo |
| 6,517,584 B1 | 2/2003 | Lecalve |
| 6,527,785 B2 | 3/2003 | Sancoff et al. |
| 6,551,241 B1 | 4/2003 | Schultz |
| 6,551,333 B2 | 4/2003 | Kuhns et al. |
| 6,558,400 B2 | 5/2003 | Deem et al. |
| 6,565,590 B2 | 5/2003 | Kieturakis et al. |
| 6,575,988 B2 | 6/2003 | Rousseau |
| 6,607,541 B1 | 8/2003 | Gardiner et al. |
| 6,610,006 B1 | 8/2003 | Amid et al. |
| 6,613,059 B2 | 9/2003 | Schaller et al. |
| 6,613,072 B2 * | 9/2003 | Lau et al. ................ 623/1.11 |
| 6,616,685 B2 | 9/2003 | Rousseau |
| 6,638,208 B1 | 10/2003 | Natarajan et al. |
| 6,638,284 B1 | 10/2003 | Rousseau et al. |
| 6,638,292 B2 | 10/2003 | Adams |
| 6,638,297 B1 | 10/2003 | Huitema |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,676,643 B2 | 1/2004 | Brushey |
| 6,689,047 B2 | 2/2004 | Gellman |
| 6,694,192 B2 | 2/2004 | Policker et al. |
| 6,695,856 B2 | 2/2004 | Kieturakis et al. |
| 6,709,442 B2 | 3/2004 | Miller et al. |
| 6,736,823 B2 | 5/2004 | Darois et al. |
| 6,736,854 B2 | 5/2004 | Vadurro et al. |
| 6,737,371 B1 | 5/2004 | Planck et al. |
| 6,746,458 B1 | 6/2004 | Cloud |
| 6,755,867 B2 | 6/2004 | Rosseau |
| 6,773,438 B1 | 8/2004 | Knodel et al. |
| 6,783,554 B2 | 8/2004 | Amara et al. |
| 6,790,213 B2 | 9/2004 | Cherok et al. |
| 6,800,081 B2 | 10/2004 | Parodi |
| 6,800,082 B2 | 10/2004 | Rousseau |
| 6,805,669 B2 | 10/2004 | Swanbom |
| 6,833,408 B2 | 12/2004 | Sehl et al. |
| 6,837,893 B2 | 1/2005 | Miller |
| 6,893,452 B2 | 5/2005 | Jacobs |
| 6,913,607 B2 | 7/2005 | Ainsworth et al. |
| 6,913,622 B2 | 7/2005 | Gjunter |
| 6,936,052 B2 | 8/2005 | Gellman et al. |
| 6,945,980 B2 | 9/2005 | Nguyen et al. |
| 6,953,428 B2 | 10/2005 | Gellman et al. |
| 6,960,217 B2 | 11/2005 | Bolduc |
| 6,960,233 B1 | 11/2005 | Berg et al. |
| 6,966,916 B2 | 11/2005 | Kumar |
| 6,974,586 B2 | 12/2005 | Greenhalgh et al. |
| 6,991,597 B2 | 1/2006 | Gellman et al. |
| 7,001,405 B2 | 2/2006 | Kieturakis et al. |
| 7,011,688 B2 | 3/2006 | Gryska et al. |
| 7,025,772 B2 | 4/2006 | Gellman et al. |
| 7,049,345 B2 | 5/2006 | Holmes-Farley |
| 7,077,850 B2 | 7/2006 | Kortenbach |
| 7,083,629 B2 | 8/2006 | Weller et al. |
| 7,083,630 B2 | 8/2006 | DeVries et al. |
| 7,094,261 B2 | 8/2006 | Zotti et al. |
| 7,101,366 B2 | 9/2006 | Trout, III et al. |

| Patent/Pub No. | Date | Name |
|---|---|---|
| 7,101,381 B2 | 9/2006 | Ford et al. |
| 7,119,062 B1 | 10/2006 | Alvis et al. |
| 7,148,315 B2 | 12/2006 | Erneta et al. |
| 7,198,046 B1 | 4/2007 | Argenta et al. |
| 7,214,236 B2 | 5/2007 | Kieturakis et al. |
| 7,216,651 B2 | 5/2007 | Argenta et al. |
| 7,220,282 B2 | 5/2007 | Kuslich |
| 7,229,452 B2 | 6/2007 | Kayan |
| 7,235,043 B2 | 6/2007 | Gellman et al. |
| 7,235,295 B2 | 6/2007 | Laurencin et al. |
| 7,255,675 B2 | 8/2007 | Gertner et al. |
| 7,320,325 B2 | 1/2008 | Duchon et al. |
| 7,331,199 B2 | 2/2008 | Ory et al. |
| 7,381,225 B2 | 6/2008 | Croce et al. |
| 7,404,819 B1 | 7/2008 | Darios et al. |
| 7,406,969 B2 | 8/2008 | Duchon et al. |
| 7,407,480 B2 | 8/2008 | Staskin et al. |
| 7,485,129 B2 * | 2/2009 | Eisenkolb ............... 606/198 |
| 7,491,232 B2 | 2/2009 | Bolduc et al. |
| 7,500,945 B2 | 3/2009 | Cox et al. |
| 7,500,993 B2 | 3/2009 | De La Torre et al. |
| 7,524,333 B2 | 4/2009 | Lambrecht et al. |
| 7,544,213 B2 | 6/2009 | Adams |
| 7,553,329 B2 | 6/2009 | Lambrecht et al. |
| 7,553,330 B2 | 6/2009 | Lambrecht et al. |
| RE40,833 E | 7/2009 | Wintermantel et al. |
| 7,566,337 B2 | 7/2009 | Sogaard-Andersen et al. |
| 7,594,921 B2 | 9/2009 | Browning |
| 7,601,118 B2 | 10/2009 | Smith et al. |
| 7,601,172 B2 | 10/2009 | Segal et al. |
| 2001/0016754 A1 | 8/2001 | Adams et al. |
| 2001/0018592 A1 | 8/2001 | Schaller et al. |
| 2001/0018593 A1 | 8/2001 | Nguyen et al. |
| 2001/0027347 A1 | 10/2001 | Rousseau |
| 2001/0044637 A1 | 11/2001 | Jacobs et al. |
| 2001/0049538 A1 | 12/2001 | Trabucco |
| 2001/0049539 A1 | 12/2001 | Rehil |
| 2001/0053919 A1 | 12/2001 | Kieturakis et al. |
| 2001/0056275 A1 | 12/2001 | Brushey |
| 2002/0010457 A1 | 1/2002 | Duchon et al. |
| 2002/0010480 A1 | 1/2002 | Sancoff et al. |
| 2002/0010490 A1 | 1/2002 | Schaller et al. |
| 2002/0010494 A1 | 1/2002 | Policker et al. |
| 2002/0029048 A1 | 3/2002 | Miller |
| 2002/0042658 A1 | 4/2002 | Tyagi |
| 2002/0049503 A1 | 4/2002 | Milbocker |
| 2002/0049504 A1 | 4/2002 | Barault |
| 2002/0052612 A1 | 5/2002 | Schmitt et al. |
| 2002/0052654 A1 | 5/2002 | Darois et al. |
| 2002/0058967 A1 | 5/2002 | Jervis |
| 2002/0065524 A1 | 5/2002 | Miller et al. |
| 2002/0066360 A1 | 6/2002 | Greenhalgh et al. |
| 2002/0077652 A1 | 6/2002 | Kieturakis et al. |
| 2002/0082621 A1 | 6/2002 | Schurr et al. |
| 2002/0087170 A1 | 7/2002 | Kuhns et al. |
| 2002/0091405 A1 | 7/2002 | Kieturakis et al. |
| 2002/0103434 A1 | 8/2002 | Swanbom |
| 2002/0103494 A1 | 8/2002 | Pacey |
| 2002/0107539 A1 | 8/2002 | Kieturakis et al. |
| 2002/0116070 A1 | 8/2002 | Amara et al. |
| 2002/0117534 A1 | 8/2002 | Green et al. |
| 2002/0147457 A1 | 10/2002 | Rosseau |
| 2002/0165561 A1 | 11/2002 | Ainsworth et al. |
| 2002/0169452 A1 | 11/2002 | Tormala et al. |
| 2002/0173803 A1 | 11/2002 | Ainsworth et al. |
| 2002/0173804 A1 | 11/2002 | Rousseau |
| 2002/0183765 A1 | 12/2002 | Adams |
| 2002/0183768 A1 | 12/2002 | Deem et al. |
| 2002/0188317 A1 | 12/2002 | Rousseau |
| 2003/0004581 A1 | 1/2003 | Rousseau |
| 2003/0039626 A1 | 2/2003 | Holmes-Farley |
| 2003/0065359 A1 | 4/2003 | Weller et al. |
| 2003/0073976 A1 | 4/2003 | Brushey |
| 2003/0078602 A1 | 4/2003 | Rousseau |
| 2003/0078603 A1 | 4/2003 | Schaller et al. |
| 2003/0105473 A1 | 6/2003 | Miller |
| 2003/0109892 A1 | 6/2003 | Deem et al. |
| 2003/0119985 A1 | 6/2003 | Sehl et al. |
| 2003/0120265 A1 | 6/2003 | Deem et al. |
| 2003/0120299 A1 | 6/2003 | Kieturakis et al. |
| 2003/0130745 A1 | 7/2003 | Cherok et al. |
| 2003/0166628 A1 | 9/2003 | Doyle et al. |
| 2003/0171761 A1 | 9/2003 | Sancoff et al. |
| 2003/0171812 A1 | 9/2003 | Grunberg et al. |
| 2003/0171823 A1 | 9/2003 | Zotti et al. |
| 2003/0187516 A1 | 10/2003 | Amid et al. |
| 2003/0195531 A1 | 10/2003 | Gardiner et al. |
| 2003/0208211 A1 | 11/2003 | Kortenbach |
| 2003/0212460 A1 | 11/2003 | Darois et al. |
| 2003/0212461 A1 | 11/2003 | Vadurro et al. |
| 2003/0212462 A1 | 11/2003 | Gryska et al. |
| 2003/0220660 A1 | 11/2003 | Kortenbach et al. |
| 2003/0225355 A1 | 12/2003 | Butler |
| 2003/0225420 A1 | 12/2003 | Wardle |
| 2004/0002679 A1 | 1/2004 | Trout et al. |
| 2004/0010317 A1 | 1/2004 | Lambrecht et al. |
| 2004/0019360 A1 | 1/2004 | Farnsworth et al. |
| 2004/0024386 A1 | 2/2004 | Deem et al. |
| 2004/0024465 A1 | 2/2004 | Lambrecht et al. |
| 2004/0030217 A1 | 2/2004 | Yeung et al. |
| 2004/0039453 A1 | 2/2004 | Anderson et al. |
| 2004/0044364 A1 | 3/2004 | DeVries et al. |
| 2004/0044412 A1 | 3/2004 | Lambrecht et al. |
| 2004/0049227 A1 | 3/2004 | Jervis |
| 2004/0049282 A1 | 3/2004 | Gjunter |
| 2004/0054376 A1 | 3/2004 | Ory et al. |
| 2004/0059356 A1 | 3/2004 | Gingras |
| 2004/0064131 A1 | 4/2004 | Brushey |
| 2004/0073237 A1 | 4/2004 | Leinsing |
| 2004/0073257 A1 | 4/2004 | Spitz |
| 2004/0082755 A1 | 4/2004 | Erneta et al. |
| 2004/0087970 A1 | 5/2004 | Chu et al. |
| 2004/0087979 A1 | 5/2004 | Field et al. |
| 2004/0087980 A1 | 5/2004 | Ford et al. |
| 2004/0092937 A1 | 5/2004 | Criscuolo et al. |
| 2004/0092969 A1 | 5/2004 | Kumar |
| 2004/0092970 A1 | 5/2004 | Xavier |
| 2004/0097924 A1 | 5/2004 | Lambrecht et al. |
| 2004/0097986 A1 | 5/2004 | Adams |
| 2004/0122452 A1 | 6/2004 | Deem et al. |
| 2004/0122453 A1 | 6/2004 | Deem et al. |
| 2004/0133214 A1 | 7/2004 | Kayan |
| 2004/0144395 A1 | 7/2004 | Evans et al. |
| 2004/0152977 A1 | 8/2004 | Duchon et al. |
| 2004/0152978 A1 | 8/2004 | Duchon et al. |
| 2004/0172048 A1 | 9/2004 | Browning |
| 2004/0181288 A1 | 9/2004 | Darois et al. |
| 2004/0193043 A1 | 9/2004 | Duchon et al. |
| 2004/0215219 A1 | 10/2004 | Eldridge et al. |
| 2004/0225247 A1 | 11/2004 | Pugsley et al. |
| 2004/0225373 A1 | 11/2004 | Pugsley et al. |
| 2004/0230208 A1 | 11/2004 | Shayani |
| 2004/0234576 A1 | 11/2004 | Martin et al. |
| 2004/0249412 A1 | 12/2004 | Snow et al. |
| 2004/0254592 A1 | 12/2004 | DiCarlo et al. |
| 2005/0004427 A1 | 1/2005 | Cervigni |
| 2005/0010239 A1 | 1/2005 | Chefitz |
| 2005/0010306 A1 | 1/2005 | Priewe et al. |
| 2005/0015102 A1 | 1/2005 | Chefitz |
| 2005/0019436 A1 | 1/2005 | Burch et al. |
| 2005/0021058 A1 | 1/2005 | Negro |
| 2005/0027369 A1 | 2/2005 | Eldridge et al. |
| 2005/0033318 A1 | 2/2005 | Miller et al. |
| 2005/0038452 A1 | 2/2005 | Chu |
| 2005/0054771 A1 | 3/2005 | Sehl et al. |
| 2005/0055097 A1 | 3/2005 | Grunberg et al. |
| 2005/0060038 A1 | 3/2005 | Lambrecht et al. |
| 2005/0065072 A1 | 3/2005 | Keeler et al. |
| 2005/0075667 A1 | 4/2005 | Schaller et al. |
| 2005/0080454 A1 | 4/2005 | Drews et al. |
| 2005/0113849 A1 | 5/2005 | Popadiuk et al. |
| 2005/0113858 A1 | 5/2005 | Deutsch |
| 2005/0118239 A1 | 6/2005 | Sabesan |
| 2005/0129733 A1 | 6/2005 | Milbocker et al. |
| 2005/0142315 A1 | 6/2005 | DeSimone et al. |
| 2005/0143817 A1 | 6/2005 | Hunter et al. |
| 2005/0149072 A1 | 7/2005 | DeVries et al. |
| 2005/0149080 A1 | 7/2005 | Hunter et al. |

| Publication No. | Date | Inventor |
|---|---|---|
| 2005/0149158 A1 | 7/2005 | Hunter et al. |
| 2005/0154361 A1 | 7/2005 | Sabesan |
| 2005/0159777 A1 | 7/2005 | Spitz |
| 2005/0165425 A1 | 7/2005 | Croce et al. |
| 2005/0165488 A1 | 7/2005 | Hunter et al. |
| 2005/0169959 A1 | 8/2005 | Hunter et al. |
| 2005/0175663 A1 | 8/2005 | Hunter et al. |
| 2005/0177225 A1 | 8/2005 | Hunter et al. |
| 2005/0181008 A1 | 8/2005 | Hunter et al. |
| 2005/0181011 A1 | 8/2005 | Hunter et al. |
| 2005/0181977 A1 | 8/2005 | Hunter et al. |
| 2005/0183728 A1 | 8/2005 | Hunter et al. |
| 2005/0191331 A1 | 9/2005 | Hunter et al. |
| 2005/0192600 A1 | 9/2005 | Nicolo et al. |
| 2005/0202067 A1 | 9/2005 | Lendlein et al. |
| 2005/0222591 A1 | 10/2005 | Gingras et al. |
| 2005/0228408 A1 | 10/2005 | Fricke et al. |
| 2005/0234557 A1 | 10/2005 | Lambrecht et al. |
| 2005/0240269 A1 | 10/2005 | Lambrecht et al. |
| 2005/0244455 A1 | 11/2005 | Greenawalt |
| 2005/0245787 A1 | 11/2005 | Cox et al. |
| 2005/0249770 A1 | 11/2005 | Hunter |
| 2005/0267325 A1 | 12/2005 | Bouchier et al. |
| 2005/0271794 A1 | 12/2005 | DeSimone et al. |
| 2005/0273146 A1 | 12/2005 | DeSimone et al. |
| 2005/0283189 A1 | 12/2005 | Rosenblatt |
| 2005/0283190 A1 | 12/2005 | Huitema et al. |
| 2005/0283246 A1 | 12/2005 | Cauthen et al. |
| 2005/0283962 A1 | 12/2005 | Boudjemline |
| 2005/0288691 A1 | 12/2005 | Leiboff |
| 2005/0288775 A1 | 12/2005 | Dong |
| 2006/0009802 A1 | 1/2006 | Modesitt |
| 2006/0015142 A1 | 1/2006 | Malazgirt |
| 2006/0015143 A1 | 1/2006 | Alvarado |
| 2006/0024238 A1 | 2/2006 | Barth et al. |
| 2006/0025649 A1 | 2/2006 | Smith et al. |
| 2006/0039896 A1 | 2/2006 | Kleinsek et al. |
| 2006/0047180 A1 | 3/2006 | Hegde et al. |
| 2006/0052816 A1 | 3/2006 | Bates et al. |
| 2006/0064175 A1 | 3/2006 | Pelissier et al. |
| 2006/0079558 A1 | 4/2006 | Aberg et al. |
| 2006/0079559 A1 | 4/2006 | Aberg et al. |
| 2006/0083710 A1 | 4/2006 | Joerger et al. |
| 2006/0105026 A1 | 5/2006 | Fortune et al. |
| 2006/0116696 A1 | 6/2006 | Odermatt et al. |
| 2006/0122637 A1 | 6/2006 | Barker |
| 2006/0127353 A1 | 6/2006 | Holmes-Farley |
| 2006/0129152 A1 | 6/2006 | Shipp |
| 2006/0129154 A1 | 6/2006 | Shipp |
| 2006/0142787 A1 | 6/2006 | Weller et al. |
| 2006/0147488 A1 | 7/2006 | Wohlert |
| 2006/0147492 A1 | 7/2006 | Hunter et al. |
| 2006/0149316 A1 | 7/2006 | DeVries et al. |
| 2006/0155165 A1 | 7/2006 | Vanden Hoek et al. |
| 2006/0155379 A1 | 7/2006 | Heneveld et al. |
| 2006/0177489 A1 | 8/2006 | Massouda et al. |
| 2006/0189918 A1 | 8/2006 | Barker |
| 2006/0200246 A1 | 9/2006 | Lambrecht et al. |
| 2006/0206118 A1 | 9/2006 | Kim et al. |
| 2006/0206178 A1 | 9/2006 | Kim |
| 2006/0210602 A1 | 9/2006 | Sehl et al. |
| 2006/0217812 A1 | 9/2006 | Lambrecht et al. |
| 2006/0228391 A1 | 10/2006 | Seyedin et al. |
| 2006/0233852 A1 | 10/2006 | Milbocker |
| 2006/0240063 A9 | 10/2006 | Hunter et al. |
| 2006/0251702 A1 | 11/2006 | Janis et al. |
| 2006/0253203 A1 | 11/2006 | Alvarado |
| 2006/0264698 A1 | 11/2006 | Kondonis et al. |
| 2006/0282103 A1 | 12/2006 | Fricke et al. |
| 2006/0282105 A1 | 12/2006 | Ford et al. |
| 2006/0287729 A1 | 12/2006 | Segal et al. |
| 2006/0287730 A1 | 12/2006 | Segal et al. |
| 2007/0016300 A1 | 1/2007 | Kuslich |
| 2007/0021756 A1 | 1/2007 | Kortenbach |
| 2007/0026043 A1 | 2/2007 | Guan et al. |
| 2007/0027358 A1 | 2/2007 | Gertner et al. |
| 2007/0032881 A1 | 2/2007 | Browning |
| 2007/0036876 A1 | 2/2007 | Burch et al. |
| 2007/0038220 A1 | 2/2007 | Shipp |
| 2007/0038310 A1 | 2/2007 | Guetty |
| 2007/0100355 A1 | 5/2007 | Bonde et al. |
| 2007/0110786 A1 | 5/2007 | Tenney et al. |
| 2007/0111937 A1 | 5/2007 | Pickar et al. |
| 2007/0118133 A1 | 5/2007 | Lambrecht et al. |
| 2007/0118158 A1 | 5/2007 | Deem et al. |
| 2007/0118159 A1 | 5/2007 | Deem et al. |
| 2007/0122425 A1 | 5/2007 | Keeler et al. |
| 2007/0134292 A1 | 6/2007 | Suokas et al. |
| 2007/0135929 A1 | 6/2007 | Williams et al. |
| 2007/0156245 A1 | 7/2007 | Cauthen et al. |
| 2007/0162030 A1 | 7/2007 | Aranyi et al. |
| 2007/0162135 A1 | 7/2007 | Segal et al. |
| 2007/0167963 A1 | 7/2007 | Deem et al. |
| 2007/0173864 A1 | 7/2007 | Chu |
| 2007/0173888 A1 | 7/2007 | Gertner et al. |
| 2007/0179335 A1 | 8/2007 | Gertner et al. |
| 2007/0184277 A1 | 8/2007 | Schussler et al. |
| 2007/0185506 A1 | 8/2007 | Jackson |
| 2007/0185541 A1 | 8/2007 | DiUbaldi et al. |
| 2007/0198040 A1 | 8/2007 | Buevich et al. |
| 2007/0202148 A1 | 8/2007 | Ringeisen et al. |
| 2007/0202173 A1 | 8/2007 | Cueto-Garcia |
| 2007/0203507 A1 | 8/2007 | McLaughlin et al. |
| 2007/0207186 A1 | 9/2007 | Scanlon et al. |
| 2007/0208358 A1 | 9/2007 | Kayan |
| 2007/0219569 A1 | 9/2007 | Shayani |
| 2007/0225791 A1 | 9/2007 | Molitor et al. |
| 2007/0244502 A1 | 10/2007 | Deutsch |
| 2007/0250147 A1 | 10/2007 | Walther et al. |
| 2007/0260179 A1 | 11/2007 | Sholev et al. |
| 2007/0260268 A1 | 11/2007 | Bartee et al. |
| 2007/0265710 A1 | 11/2007 | Brown et al. |
| 2007/0270752 A1 | 11/2007 | LaBombard |
| 2007/0280990 A1 | 12/2007 | Stopek |
| 2007/0293717 A1 | 12/2007 | Kaleta et al. |
| 2007/0293878 A1 | 12/2007 | Butsch |
| 2007/0299300 A1 | 12/2007 | Smith et al. |
| 2007/0299542 A1 | 12/2007 | Mathisen et al. |
| 2008/0015501 A1 | 1/2008 | Gertner |
| 2008/0021545 A1 | 1/2008 | Reneker et al. |
| 2008/0033461 A1 | 2/2008 | Koeckerling et al. |
| 2008/0035243 A1 | 2/2008 | Breitenkamp et al. |
| 2008/0045952 A1 | 2/2008 | Kuslich |
| 2008/0065229 A1 | 3/2008 | Adams |
| 2008/0086216 A1 | 4/2008 | Wilson et al. |
| 2008/0091222 A1 | 4/2008 | Deusch et al. |
| 2008/0091276 A1 | 4/2008 | Deusch et al. |
| 2008/0103351 A1 | 5/2008 | Montpetit et al. |
| 2008/0113035 A1 | 5/2008 | Hunter |
| 2008/0125869 A1 | 5/2008 | Paz et al. |
| 2008/0131509 A1 | 6/2008 | Hossainy et al. |
| 2008/0132602 A1 | 6/2008 | Rizk et al. |
| 2008/0147198 A1 | 6/2008 | Cherok et al. |
| 2008/0147200 A1 | 6/2008 | Rousseau et al. |
| 2008/0167519 A1 | 7/2008 | St-Germain |
| 2008/0167667 A1 | 7/2008 | Criscuolo et al. |
| 2008/0167668 A1 | 7/2008 | Criscuolo et al. |
| 2008/0188874 A1 | 8/2008 | Henderson |
| 2008/0193494 A1 | 8/2008 | Sabesan |
| 2008/0195121 A1 | 8/2008 | Eldar et al. |
| 2008/0200979 A1 | 8/2008 | Dieck et al. |
| 2008/0215154 A1 | 9/2008 | Lambrecht et al. |
| 2008/0243149 A1 | 10/2008 | Kockerling et al. |
| 2008/0255593 A1 | 10/2008 | St-Germain |
| 2008/0260794 A1 | 10/2008 | Lauritzen et al. |
| 2008/0269896 A1 | 10/2008 | Cherok et al. |
| 2008/0281433 A1 | 11/2008 | Chang et al. |
| 2008/0287970 A1 | 11/2008 | Amato et al. |
| 2008/0306497 A1 | 12/2008 | Brown et al. |
| 2008/0312751 A1 | 12/2008 | Pugsley et al. |
| 2009/0004239 A1 | 1/2009 | Ladet et al. |
| 2009/0005867 A1 | 1/2009 | Lefranc et al. |
| 2009/0012350 A1 | 1/2009 | Tihon |
| 2009/0012546 A1 | 1/2009 | N'diaye et al. |
| 2009/0018559 A1 | 1/2009 | Buevich et al. |
| 2009/0030434 A1 | 1/2009 | Paz et al. |
| 2009/0030522 A1 | 1/2009 | Cauthen, III et al. |
| 2009/0030527 A1 | 1/2009 | Richter |

| | | | | | | |
|---|---|---|---|---|---|---|
| 2009/0036937 A1 | 2/2009 | Cauthen, III et al. | EP | 1674048 A1 | 6/2006 |
| 2009/0036989 A1 | 2/2009 | Cauthen, III et al. | EP | 1274473 B1 | 7/2006 |
| 2009/0036990 A1 | 2/2009 | Cauthen, III et al. | EP | 0934024 B1 | 8/2006 |
| 2009/0036996 A1 | 2/2009 | Roeber | EP | 1503683 B1 | 8/2006 |
| 2009/0062823 A1 | 3/2009 | Richter | EP | 1700579 A1 | 9/2006 |
| 2009/0069826 A1 | 3/2009 | Walther et al. | EP | 1704832 A2 | 9/2006 |
| 2009/0105526 A1 | 4/2009 | Piroli Torelli et al. | EP | 200614650 A2 | 10/2006 |
| 2009/0125041 A1 | 5/2009 | Dudai | EP | 1079741 B1 | 11/2006 |
| 2009/0137864 A1 | 5/2009 | Cox et al. | EP | 0964645 B1 | 7/2007 |
| 2009/0149875 A1 | 6/2009 | Abele et al. | EP | 1163019 B1 | 10/2007 |
| 2009/0155332 A1 | 6/2009 | Sherry et al. | EP | 1849440 A1 | 10/2007 |
| 2009/0157184 A1 | 6/2009 | Cauthen, III et al. | EP | 1867348 A2 | 12/2007 |
| 2009/0157195 A1 | 6/2009 | Siedle | EP | 1870056 A1 | 12/2007 |
| 2009/0162273 A1 | 6/2009 | Lawrynowicz et al. | EP | 1531739 B1 | 2/2008 |
| 2009/0182190 A1 | 7/2009 | Dann | EP | 1406557 B1 | 11/2008 |
| 2009/0182352 A1 | 7/2009 | Paz et al. | EP | 1990014 A2 | 11/2008 |
| 2009/0187258 A1 | 7/2009 | Ip et al. | EP | 2002800 A1 | 12/2008 |
| 2009/0192346 A1 | 7/2009 | Rosenblatt | EP | 1505927 B1 | 1/2009 |
| 2009/0192528 A1 | 7/2009 | Higgins et al. | EP | 1372525 B1 | 3/2009 |
| 2009/0198260 A1 | 8/2009 | Ford et al. | EP | 1653880 B1 | 4/2009 |
| 2009/0204130 A1 | 8/2009 | Kantsevoy et al. | EP | 2050474 A2 | 4/2009 |
| 2009/0204227 A1 | 8/2009 | Derwin et al. | EP | 1940312 B1 | 7/2009 |
| 2009/0216075 A1 | 8/2009 | Bell et al. | FR | 2789888 A1 | 8/2000 |
| 2009/0216104 A1 | 8/2009 | DeSimone et al. | WO | WO8204390 A1 | 12/1982 |
| 2009/0216338 A1 | 8/2009 | Gingras et al. | WO | WO92/06639 | 4/1992 |
| 2009/0234379 A1 | 9/2009 | Rehnke | WO | WO9206639 A2 | 4/1992 |
| 2009/0234461 A1 | 9/2009 | Rehnke | WO | WO9211824 A1 | 7/1992 |
| 2009/0240342 A1 | 9/2009 | Lindh et al. | WO | WO9219162 A2 | 11/1992 |
| 2009/0240343 A1 | 9/2009 | Adams | WO | WO9221293 A1 | 12/1992 |
| 2009/0248048 A1 | 10/2009 | Milbocker | WO | WO9303685 A1 | 3/1993 |
| 2009/0254103 A1 | 10/2009 | Deutsch | WO | WO9309722 A1 | 5/1993 |
| 2009/0259094 A1 | 10/2009 | Bouchier et al. | WO | WO9317635 A1 | 9/1993 |
| | | | WO | WO9417747 A1 | 8/1994 |
| FOREIGN PATENT DOCUMENTS | | | WO | WO9419029 A1 | 9/1994 |
| EP | 0328421 A2 | 8/1989 | WO | WO9427535 A1 | 12/1994 |
| EP | 0525791 A1 | 2/1993 | WO | WO95/30374 | 11/1995 |
| EP | 0537769 A1 | 4/1993 | WO | WO9530374 A1 | 11/1995 |
| EP | 0544485 A1 | 6/1993 | WO | WO9531140 A1 | 11/1995 |
| EP | 0556018 A1 | 8/1993 | WO | WO9603091 A1 | 2/1996 |
| EP | 0557964 A1 | 9/1993 | WO | WO9603165 A1 | 2/1996 |
| EP | 0573273 | 12/1993 | WO | WO9606634 A1 | 3/1996 |
| EP | 0573273 A2 | 12/1993 | WO | WO9609795 A1 | 4/1996 |
| EP | 0579377 A2 | 1/1994 | WO | WO9640307 A1 | 12/1996 |
| EP | 0581036 | 2/1994 | WO | WO9702789 A1 | 1/1997 |
| EP | 0581036 A1 | 2/1994 | WO | WO9722371 A1 | 6/1997 |
| EP | 0614650 A2 | 9/1994 | WO | WO9732526 A1 | 9/1997 |
| EP | 0702934A1 | 3/1996 | WO | WO9735533 A1 | 10/1997 |
| EP | 0744162 A2 | 11/1996 | WO | WO9803713 A1 | 1/1998 |
| EP | 0519022 B1 | 12/1997 | WO | WO9811814 | 3/1998 |
| EP | 0827724 A2 | 3/1998 | WO | WO9814134 A2 | 4/1998 |
| EP | 0553344 B1 | 9/1998 | WO | WO9816153 A1 | 4/1998 |
| EP | 0746258 B1 | 9/1998 | WO | WO9903422 A1 | 1/1999 |
| EP | 0898944 A2 | 3/1999 | WO | WO9905992 A1 | 2/1999 |
| EP | 0908482 A1 | 4/1999 | WO | WO9916381 A1 | 4/1999 |
| EP | 0986993 A1 | 3/2000 | WO | WO9951163 A1 | 10/1999 |
| EP | 0837660 B1 | 5/2000 | WO | WO9960931 A1 | 12/1999 |
| EP | 1060714 A2 | 12/2000 | WO | WO9962406 A2 | 12/1999 |
| EP | 1145693 A2 | 10/2001 | WO | WO9963051 A2 | 12/1999 |
| EP | 1181899 A2 | 2/2002 | WO | WO0007520 A1 | 2/2000 |
| EP | 1199037 A2 | 4/2002 | WO | WO0016822 A2 | 3/2000 |
| EP | 1199038 A2 | 4/2002 | WO | WO0056376 A1 | 9/2000 |
| EP | 1219265 | 7/2002 | WO | WO0057796 A1 | 10/2000 |
| EP | 1219265 A2 | 7/2002 | WO | WO0057812 A1 | 10/2000 |
| EP | 0746267 B1 | 11/2002 | WO | WO0061033 | 10/2000 |
| EP | 1018980 B1 | 1/2003 | WO | WO0067663 A1 | 11/2000 |
| EP | 1306061 A2 | 5/2003 | WO | WO0071548 A1 | 11/2000 |
| EP | 1317904 A1 | 6/2003 | WO | WO0071549 A1 | 11/2000 |
| EP | 1366717 A1 | 12/2003 | WO | WO0108594 A1 | 2/2001 |
| EP | 0783270 B1 | 6/2004 | WO | WO0126588 A2 | 4/2001 |
| EP | 1200010 B1 | 3/2005 | WO | WO0154589 A1 | 8/2001 |
| EP | 1164967 B1 | 5/2005 | WO | WO0168653 A1 | 9/2001 |
| EP | 1541183 A1 | 6/2005 | WO | WO0170322 A1 | 9/2001 |
| EP | WO2005082273 A1 | 9/2005 | WO | WO0180788 A2 | 11/2001 |
| EP | 0828453 B1 | 11/2005 | WO | WO0185058 A2 | 11/2001 |
| EP | 1001717 B1 | 11/2005 | WO | WO0185060 | 11/2001 |
| EP | 1303230 B1 | 11/2005 | WO | WO0189390 A1 | 11/2001 |
| EP | 1607048 A1 | 12/2005 | WO | WO0189392 A2 | 11/2001 |
| EP | 1404250 B1 | 2/2006 | WO | WO0207648 A1 | 1/2002 |
| EP | 1671604 A2 | 6/2006 | WO | WO0217771 A2 | 3/2002 |

| | | | | | | |
|---|---|---|---|---|---|---|
| WO | WO0217796 A1 | 3/2002 | | WO | WO2005079335 A2 | 9/2005 |
| WO | WO0217797 A1 | 3/2002 | | WO | WO2005082274 A1 | 9/2005 |
| WO | WO0219916 A1 | 3/2002 | | WO | WO2005094721 A1 | 10/2005 |
| WO | WO0219923 A1 | 3/2002 | | WO | WO2005099628 A2 | 10/2005 |
| WO | WO0222047 A1 | 3/2002 | | WO | WO2005102209 A1 | 11/2005 |
| WO | WO0224080 A2 | 3/2002 | | WO | WO2005105172 A1 | 11/2005 |
| WO | WO0226747 A1 | 4/2002 | | WO | WO2005110243 A2 | 11/2005 |
| WO | WO0230336 A2 | 4/2002 | | WO | WO2005110273 A1 | 11/2005 |
| WO | WO0232346 A1 | 4/2002 | | WO | WO2006002439 A1 | 1/2006 |
| WO | WO0234140 A2 | 5/2002 | | WO | WO2006008429 A1 | 1/2006 |
| WO | WO0235990 A2 | 5/2002 | | WO | WO2006012353 A2 | 2/2006 |
| WO | WO02058543 A2 | 8/2002 | | WO | WO2006013337 A2 | 2/2006 |
| WO | WO02078568 A1 | 10/2002 | | WO | WO2006015031 A2 | 2/2006 |
| WO | WO02080779 A1 | 10/2002 | | WO | WO2006026509 A2 | 3/2006 |
| WO | WO02080780 A1 | 10/2002 | | WO | WO2006034117 A1 | 3/2006 |
| WO | WO02087425 A2 | 11/2002 | | WO | WO2006036936 A2 | 4/2006 |
| WO | WO02091928 A1 | 11/2002 | | WO | WO2006037047 A2 | 4/2006 |
| WO | WO02091953 A1 | 11/2002 | | WO | WO2006040760 A2 | 4/2006 |
| WO | WO02096327 A2 | 12/2002 | | WO | WO2006044785 A1 | 4/2006 |
| WO | WO03002029 A1 | 1/2003 | | WO | WO2006047645 A2 | 5/2006 |
| WO | WO03002130 A1 | 1/2003 | | WO | WO2006048885 A1 | 5/2006 |
| WO | WO03032867 A1 | 4/2003 | | WO | WO2006/082587 | 8/2006 |
| WO | WO03059180 A2 | 7/2003 | | WO | WO2006082587 A2 | 8/2006 |
| WO | WO03059201 A1 | 7/2003 | | WO | WO2006086339 A2 | 8/2006 |
| WO | WO03059217 A1 | 7/2003 | | WO | WO2006092159 A1 | 9/2006 |
| WO | WO03077730 A2 | 9/2003 | | WO | WO2006092236 A1 | 9/2006 |
| WO | WO03082125 A1 | 10/2003 | | WO | WO2006102457 A2 | 9/2006 |
| WO | WO03084410 A1 | 10/2003 | | WO | WO2006116000 A2 | 11/2006 |
| WO | WO03088846 A1 | 10/2003 | | WO | WO2006119034 A2 | 11/2006 |
| WO | WO03090633 A2 | 11/2003 | | WO | WO2007004228 A1 | 1/2007 |
| WO | WO03092509 A1 | 11/2003 | | WO | WO2007011689 A2 | 1/2007 |
| WO | WO03094781 A1 | 11/2003 | | WO | WO2007017872 A2 | 2/2007 |
| WO | WO03094783 A1 | 11/2003 | | WO | WO2007021620 A2 | 2/2007 |
| WO | WO03094786 A1 | 11/2003 | | WO | WO2007021759 A2 | 2/2007 |
| WO | WO03094787 A1 | 11/2003 | | WO | WO2007021834 A1 | 2/2007 |
| WO | WO03096909 A1 | 11/2003 | | WO | WO2007/030676 | 3/2007 |
| WO | WO03096929 A1 | 11/2003 | | WO | WO2007025293 A2 | 3/2007 |
| WO | WO03097011 A1 | 11/2003 | | WO | WO2007025296 A2 | 3/2007 |
| WO | WO03099160 A1 | 12/2003 | | WO | WO2007025302 A2 | 3/2007 |
| WO | WO03103473 A2 | 12/2003 | | WO | WO2007030676 A2 | 3/2007 |
| WO | WO2004004600 A1 | 1/2004 | | WO | WO2007034145 A2 | 3/2007 |
| WO | WO2004006808 A2 | 1/2004 | | WO | WO2007050382 A1 | 5/2007 |
| WO | WO2004012579 A2 | 2/2004 | | WO | WO2007051221 A1 | 5/2007 |
| WO | WO2004012627 A1 | 2/2004 | | WO | WO2007055755 A1 | 5/2007 |
| WO | WO2004019787 A2 | 3/2004 | | WO | WO2007070141 A1 | 6/2007 |
| WO | WO2004024030 A1 | 3/2004 | | WO | WO2007072469 A2 | 6/2007 |
| WO | WO2004034924 A2 | 4/2004 | | WO | WO2007081955 A1 | 7/2007 |
| WO | WO2004/037123 | 5/2004 | | WO | WO2007087132 A1 | 8/2007 |
| WO | WO2004037123 A1 | 5/2004 | | WO | WO2007087146 A2 | 8/2007 |
| WO | WO2004058286 A1 | 7/2004 | | WO | WO2007115110 A2 | 10/2007 |
| WO | WO2004060425 A2 | 7/2004 | | WO | WO2007129220 A2 | 11/2007 |
| WO | WO2004062529 A2 | 7/2004 | | WO | WO2007133311 A2 | 11/2007 |
| WO | WO2004062530 A1 | 7/2004 | | WO | WO2007136820 A2 | 11/2007 |
| WO | WO2004028547 A1 | 8/2004 | | WO | WO2007137211 A2 | 11/2007 |
| WO | WO2004069866 A1 | 8/2004 | | WO | WO2007143726 A2 | 12/2007 |
| WO | WO2004/080348 | 9/2004 | | WO | WO2007144782 A2 | 12/2007 |
| WO | WO2004080348 A1 | 9/2004 | | WO | WO2007146784 A2 | 12/2007 |
| WO | WO2004087227 A1 | 10/2004 | | WO | WO2008006097 A2 | 1/2008 |
| WO | WO2004093737 A1 | 11/2004 | | WO | WO2008016802 A1 | 2/2008 |
| WO | WO2004098461 A2 | 11/2004 | | WO | WO2008026905 A2 | 3/2008 |
| WO | WO2004098665 A1 | 11/2004 | | WO | WO2008030873 A2 | 3/2008 |
| WO | WO2004100841 A1 | 11/2004 | | WO | WO2008030939 A2 | 3/2008 |
| WO | WO2004101002 A2 | 11/2004 | | WO | WO2008/045635 | 4/2008 |
| WO | WO2004103166 A2 | 12/2004 | | WO | WO2008045635 A2 | 4/2008 |
| WO | WO2004103414 A2 | 12/2004 | | WO | WO2008055028 A1 | 5/2008 |
| WO | WO2005003351 A1 | 1/2005 | | WO | WO2008065653 A1 | 6/2008 |
| WO | WO2005004727 A1 | 1/2005 | | WO | WO2008069919 A2 | 6/2008 |
| WO | WO2005007209 A1 | 1/2005 | | WO | WO2008083484 A1 | 7/2008 |
| WO | WO2005014634 A1 | 2/2005 | | WO | WO2008085825 A1 | 7/2008 |
| WO | WO2005018494 A1 | 3/2005 | | WO | WO2008/099382 | 8/2008 |
| WO | WO2005019241 A2 | 3/2005 | | WO | WO2008094217 A1 | 8/2008 |
| WO | WO2005019315 A1 | 3/2005 | | WO | WO2008094842 A1 | 8/2008 |
| WO | WO2005035548 A1 | 4/2005 | | WO | WO2008099382 A1 | 8/2008 |
| WO | WO2005041784 A2 | 5/2005 | | WO | WO2008112437 A2 | 9/2008 |
| WO | WO2005044143 A1 | 5/2005 | | WO | WO2008124056 A1 | 10/2008 |
| WO | WO2005051172 A2 | 6/2005 | | WO | WO2008140989 A2 | 11/2008 |
| WO | WO2005055958 A2 | 6/2005 | | WO | WO2008157497 A2 | 12/2008 |
| WO | WO2005065324 A2 | 7/2005 | | WO | WO2008157777 A1 | 12/2008 |
| WO | WO2005065552 A2 | 7/2005 | | WO | WO2009005625 A1 | 1/2009 |

| | | | |
|---|---|---|---|
| WO | WO2009005634 A1 | 1/2009 |
| WO | WO2009011824 A1 | 1/2009 |
| WO | WO2009012001 A1 | 1/2009 |
| WO | WO2009022348 A1 | 2/2009 |
| WO | WO2009036094 A2 | 3/2009 |
| WO | WO2009039371 A1 | 3/2009 |
| WO | WO2009/050717 | 4/2009 |
| WO | WO2009042442 A1 | 4/2009 |
| WO | WO2009048314 A1 | 4/2009 |
| WO | WO2009050717 A2 | 4/2009 |
| WO | WO2009059005 A1 | 5/2009 |
| WO | WO2009064845 A2 | 5/2009 |
| WO | WO2009069119 A1 | 6/2009 |
| WO | WO2009075786 A1 | 6/2009 |
| WO | WO2009075932 A1 | 6/2009 |
| WO | WO2009075933 A1 | 6/2009 |
| WO | WO2009092294 A1 | 7/2009 |
| WO | WO2009086446 A1 | 7/2009 |
| WO | WO2009094015 A1 | 7/2009 |
| WO | WO2009097380 A1 | 8/2009 |
| WO | WO2009102792 A2 | 8/2009 |
| WO | WO2009104182 A2 | 8/2009 |
| WO | WO2009113972 A2 | 9/2009 |
| WO | WO2009126781 A1 | 10/2009 |

* cited by examiner

DEVICE AND METHOD FOR ROLLING AND INSERTING A PROSTHETIC PATCH INTO A BODY CAVITY

RELATED APPLICATIONS

The present application is a continuation-in-part of U.S. patent application Ser. No. 12/834,456, filed Jul. 12, 2010, which is a continuation-in-part of PCT international patent application number PCT/IL2009/000188, filed Feb. 18, 2009, which claims the benefit of and priority to U.S. provisional patent application Ser. No. 61/029,386, filed Feb. 18, 2008. The present application also claims the benefit of and priority to U.S. provisional patent application Ser. No. 61/300,455, filed Feb. 2, 2010. The content of each of these is incorporated by reference herein in its entirety.

FIELD OF THE INVENTION

This invention generally relates to minimal invasive surgery. More specifically the current invention relates to an apparatus especially adapted to fold prosthetic patches and to insert said patches into a body cavity through a cannula or an incision.

BACKGROUND OF THE INVENTION

An object of the present invention is to provide apparatus and a method for performing corrective surgery on internal wounds such as hernia where invasion of the patient's body tissues is minimized and resultant trauma is reduced.

A hernia is a protrusion of a tissue, structure, or part of an organ through the muscular tissue or the membrane by which it is normally contained. In other words a hernia is a defect in the abdominal wall through which a portion of the intra-abdominal contents can protrude. This often causes discomfort and an unsightly, visible bulge in the abdomen. When such a hernia defect occurs in the abdominal region, conventional corrective surgery has required opening the abdominal cavity by surgical incision through the major abdominal muscles. While this technique provides for effective corrective surgery of the hernia defect, it has the disadvantage of requiring a hospital stay of as much as a week, during which pain is frequently intense, and it requires an extended period of recuperation. After the conventional surgery patients frequently cannot return to a full range of activity and work schedule for a month or more. Accordingly, medical science has sought alternative techniques that are less traumatic to the patient and provide for more rapid recovery.

Laparoscopy is the science of introducing a viewing instrument through a port into a patient's body, typically the abdominal cavity, to view its contents. This technique has been used for diagnostic purposes for more than 75 years. Operative laparoscopy is performed through tiny openings in the abdominal wall called ports. In most surgical techniques several ports, frequently three to six, are used. Through one port is inserted the viewing device, which conventionally comprises a fiber optic rod or bundle having a video camera affixed to the outer end to receive and display images from inside the body. The various surgical instruments are inserted through other ports to do the surgery that normally would be performed through an open incision through the abdominal wall. Because the laparoscopic surgical techniques require only very small holes through the abdominal wall or other portions of the body, a patient undergoing such surgery may frequently leave the hospital within one day after the surgery and resume a full range of normal activities within a few days thereafter.

In repairing hernia the physician needs to first roll the patch in order to insert the same into the abdominal cavity.

Such rolling of the patch can be a time consuming process and sometimes even a highly difficult procedure. In addition, insufficient rolling of said patch may damage the patch during its insertion and may require operation of large forces during said insertion; such forces may lead to patient injuries and/or damage to the insertion tool.

Thus, there is still a long felt need for a device that will enable a an easy rolling of the patch prior to the insertion of the same to the abdominal cavity.

SUMMARY OF THE INVENTION

It is one object of the present invention to provide a patch rolling apparatus (PRA) adapted to enable a tight and easy rolling of a prosthetic patch onto a surgical tool such that a minimum effective cross-section of said rolled prosthetic patch perpendicular to the direction of insertion, prior to, and during, said insertion into either a cannula or an opening is obtained. Exemplary surgical tools include patch deployment devices as described in U.S. patent application Ser. No. 12/834,456, the content of which is incorporated by reference herein in its entirety.

It is another object of the present invention to provide the PRA as defined above, wherein said PRA comprises at least two sections 101 hinge-like coupled together; said PRA is characterized by at least two configurations: (i) an open configuration (OC) in which said two sections are apart to create a gap W into which said prosthetic patch can be inserted; and, (ii) a closed configuration (CC) in which said gap is minimized or eliminated such that said PRA substantially envelopes said prosthetic patch and enables said rolling of said prosthetic patch.

It is another object of the present invention to provide the PRA as defined above, additionally comprising a locking section (LS) 104 adapted to maintain said PRA 100 in its said closed configuration.

It is another object of the present invention to provide the PRA as defined above, wherein said LS comprising a locking hook 200, attached to at least one section 101 of said PRA 100 and a locking groove 105 located on the second section 101 of said PRA 100.

It is another object of the present invention to provide the PRA as defined above, wherein said LS comprising and a release tab 107 adapted to allow said release of said locking; such that once said release tab 107 is pressed said PRA is transformed into said open configuration.

It is another object of the present invention to provide the PRA as defined above, wherein said LS additionally comprising an automatic release section (ARS) which automatically releases the two sections 101 of said PRA 100 once said patch 201 is at least partially inserted into said body cavity; said ARS comprising a tilted tab 109 and pin 110.

It is another object of the present invention to provide the PRA as defined above, wherein said PRA 100 additionally comprising an anti-buckling section ABS 112 adapted to prevent buckling of said distal portion 203 of said PIS 202 during said insertion of said patch 201.

It is another object of the present invention to provide the PRA as defined above, wherein said PRA 100 additionally comprising an insertion tip 113 adapted to enable better insertion of said PRA.

It is another object of the present invention to provide a method for rolling a prosthetic patch onto a surgical tool. The method comprising steps selected inter alia from:

a. obtaining said prosthetic patch to be rolled on said surgical tool
b. obtaining a patch rolling apparatus (PRA) comprising at least two sections 101 hinge-like coupled together; said PRA is characterized by at least two configurations: (i) an open configuration (OC) in which said two sections are apart to create a gap W into which said prosthetic patch can be inserted; and, (ii) a closed configuration (CC) in which said gap is minimized or eliminated such that said PRA substantially envelopes said prosthetic patch and enables said rolling of said prosthetic patch;
c. configuring said PRA to be in said OC;
d. at least partially coupling said patch to said surgical tool;
e. inserting said surgical tool coupled to said patch into said PRA through said gap W;
f. rolling said patch inside said PRA 100 while continually transforming said PRA from its said open configuration into its said closed configuration;

It is another object of the present invention to provide the method as defined above, additionally comprising step of continue rotating said patch 201 inside said PRA 100 until the entire patch 201 in rolled inside PRA 100.

It is another object of the present invention to provide the PRA as defined above, additionally comprising step of inserting said rolled patch 201 into a body cavity through a laparoscopic cannula or through an incision.

It is another object of the present invention to provide the PRA as defined above, additionally comprising step of transforming said PRA 100 into its said open configuration and de-coupling it from said surgical tool.

It is another object of the present invention to provide the PRA as defined above, additionally comprising step of providing said PRA with a locking section (LS) 104 adapted to maintain said PRA 100 in its said closed configuration.

It is another object of the present invention to provide the PRA as defined above, additionally comprising step of providing said PRA with a release tab 107 adapted to allow said release of said locking; such that once said release tab 107 is pressed said PRA is transformed into said OC.

It is another object of the present invention to provide the PRA as defined above, additionally comprising step of providing said PRA with an automatic release section (ARS) which automatically releases the two sections 101 of said PRA 100; said ARS comprising a tilted tab 109 and pin 110.

It is still an object of the present invention to provide the PRA as defined above, additionally comprising step of providing said PRA with an anti-buckling section ABS 112.

It is lastly an object of the present invention to provide the PRA as defined above, additionally comprising step of providing said PRA with an insertion tip 113.

BRIEF DESCRIPTION OF THE DRAWINGS

The invention is herein described, by way of example only, with reference to the accompanying drawings, wherein.

DETAIL DESCRIPTION OF THE SPECIFIC EMBODIMENTS

Figure 1A:
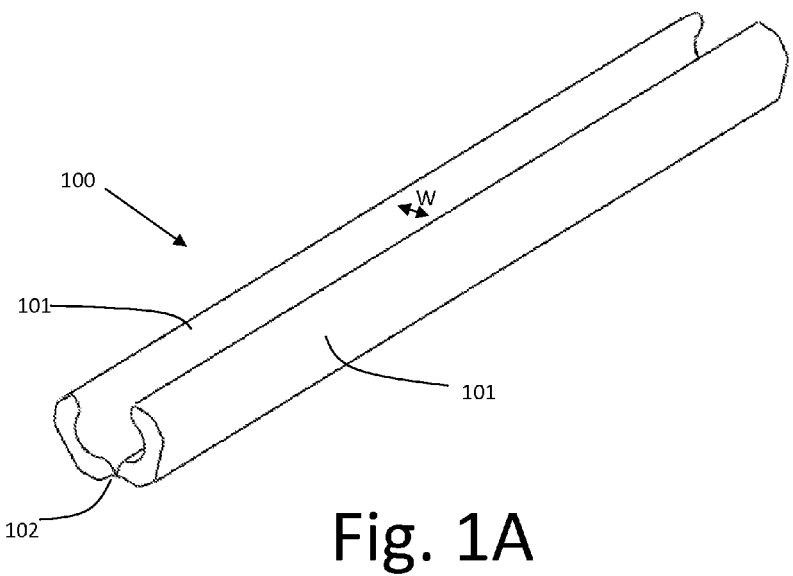
FIGS. 1A-1B illustrate a preferred embodiment of the present invention.

The following description is provided, alongside all chapters of the present invention, so as to enable any person skilled in the art to make use of the invention and sets forth the best modes contemplated by the inventor of carrying out this invention. Various modifications, however, is adapted to remain apparent to those skilled in the art, since the generic principles of the present invention have been defined specifically to provides a device and method for rolling and inserting a prosthetic patch into a body cavity.

The present invention provides a patch rolling apparatus (PRA) wherein said PRA is adapted to assist in rolling a prosthetic patch (e.g. hernia patch) onto a surgical tool (e.g. grasper, patch deployment system) such that said patch can be inserted into a body cavity (e.g. abdominal cavity) during a minimal invasive surgery.

It should be emphasized that some of the major advantages of the present invention, with respect to the prior art, is the ability roll prosthetic patches, especially large patches, faster and easier relatively to the current manual rolling manner.

Furthermore, the present invention enables an easier insertion of said patch into said body cavity relatively to the current manner.

The term "Hernia" refers hereinafter to umbilical hernia, hiatal hernia, ventral hernia, postoperative hernia, epigastric hernia, spiegelian hernia, inguinal hernia and femoral hernia, generally any abdominal wall related hernia.

The term "mesh deployment system" refers hereinafter to any device adapted to deploy a mesh/patch during a hernia surgery.

The term "hinge" or "hinge-like connection" refers hereinafter as to a type of bearing that connects two solid objects, typically allowing only a limited angle of rotation between them. Two objects connected by an ideal hinge rotate relative to each other about a fixed axis of rotation (the geometrical axis of the hinge). Hinges may be made of flexible material or of moving components. The term "hinge like connection" can refer to a standard hinge or to a living hinge (i.e., a thin flexible hinge (flexure bearing) made from plastic that joins two rigid parts together while allowing them to bend along the line of the hinge).

The term "minimally invasive surgery" refers hereinafter to procedures that avoid open invasive surgery in favor of closed or local surgery with fewer traumas. Furthermore, the term refers to a procedure that is carried out by entering the body through the skin or through a body cavity or anatomical opening, but with the smallest damage possible.

The term "pressurized body cavity" refers hereinafter to a body cavity (e.g. intraperitoneal cavity) which is insufflated by gas (e.g. $CO_2$) during a minimal invasive surgery.

The term "closed configuration" refers hereinafter to the configuration of the PRA 100 shown in FIG. 1B.

The term "open configuration" refers hereinafter to the configuration of the PRA 100 shown in FIG. 1A.

Before explaining the figures, it should be understood that the invention is not limited in its application to the details of construction and the arrangement of the components set forth in the following description or illustrated in the drawings. The invention can be carried out in various ways.

Figure 1B:
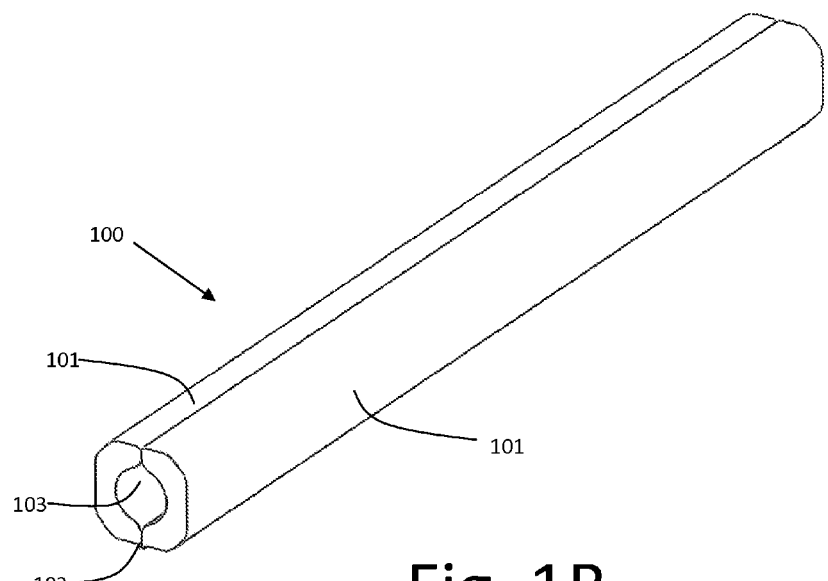

Reference is now made to FIG. 1A-1B illustrating a preferred embodiment of the present invention. According to this embodiment a patch rolling apparatus (PRA) 100 is provided. Said PRA 100 comprises two sections 101 connected to each another via a hinge 102 such that a movement of each of said sections relatively to each other is enabled along and around said hinge 102. Hinge 102 can be either a living hinge on a conventional hinge.

Said PRA 100 is characterized by two separate configurations: an open configuration (OC), as can be seen in FIG. 1A and a closed configuration (CC), as can be seen in FIG. 1B.

In the open configuration said two sections 101 are positioned apart from each other such that a gap (W) is created between them, through which a pre-rolled patch can be at least partially inserted and encapsulated within said two sections 101.

In the closed configuration said two portions 101 are substantially adjacent to one another, creating an internal cavity 103. In a preferred embodiment said cavity 103 contains no sharp edges so as to prevent any damage that may be caused to the patch during said rolling operation.

Reference is now being made to FIGS. 2A-2G illustrating a method in which said PRA 100 is utilized together with a patch introducing system 202 (PIS) in order to roll and insert a patch 201 into a body cavity of a patient during a surgery (e.g. laparoscopic hernia repair surgery).

PIS 202 is define as a surgical tool intended to insert a patch into the abdominal cavity, e.g. a patch deployment system (as illustrated in FIGS. 2A-2G), a patch introducer, a laparoscopic grasper or any combination thereof.

PIS 202 comprises a distal portion 203 (on which said patch 201 is rolled), proximal portion 204 (which is held by the surgeon) and a shaft 205 connecting said proximal portion 204 and distal portion 203 together.

Figure 2A:
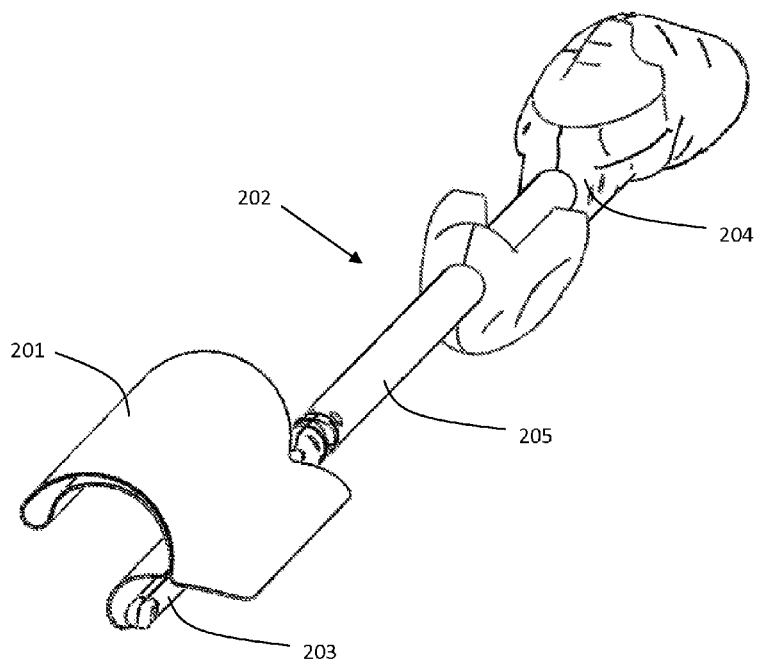
FIGS. 2A-2G illustrate a method in which said PRA 100 is being utilized together with a patch introducing system 202 (PIS).
Figure 2B:
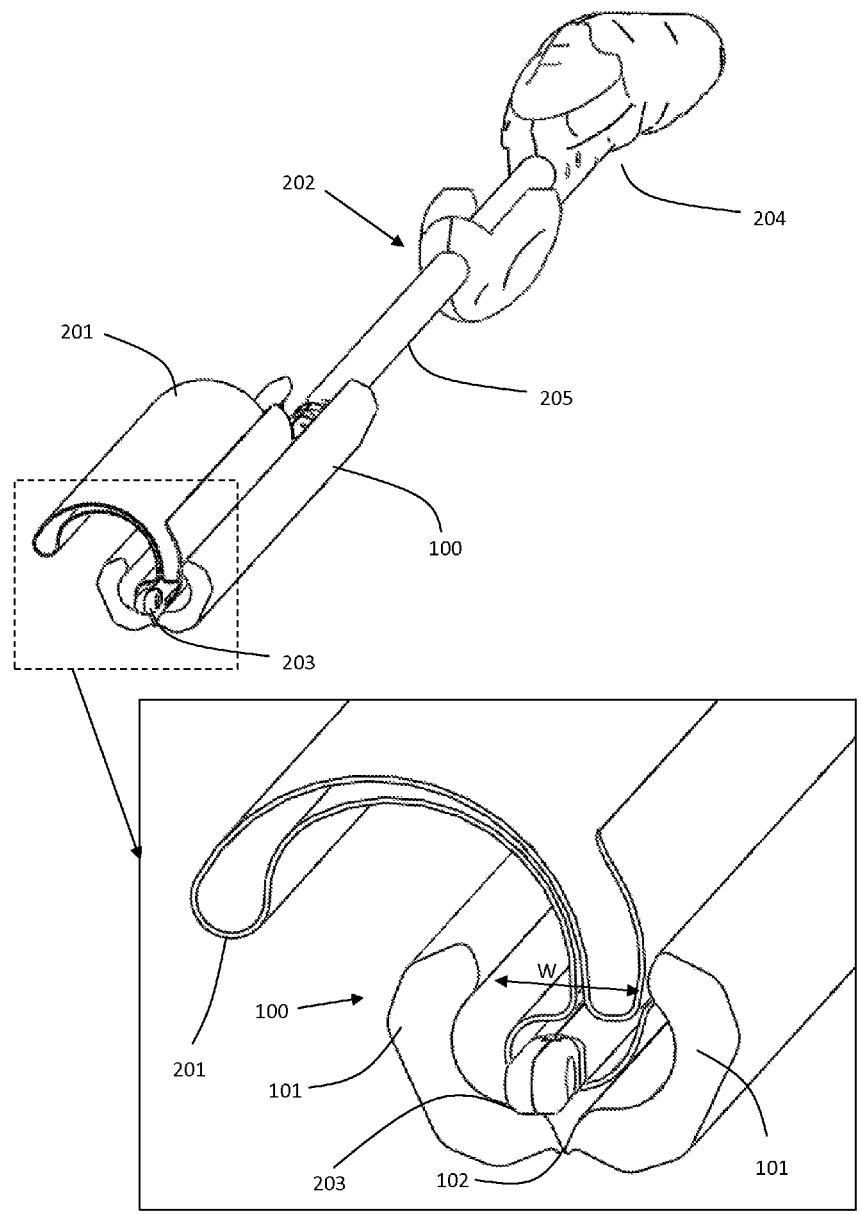
Figure 2C:
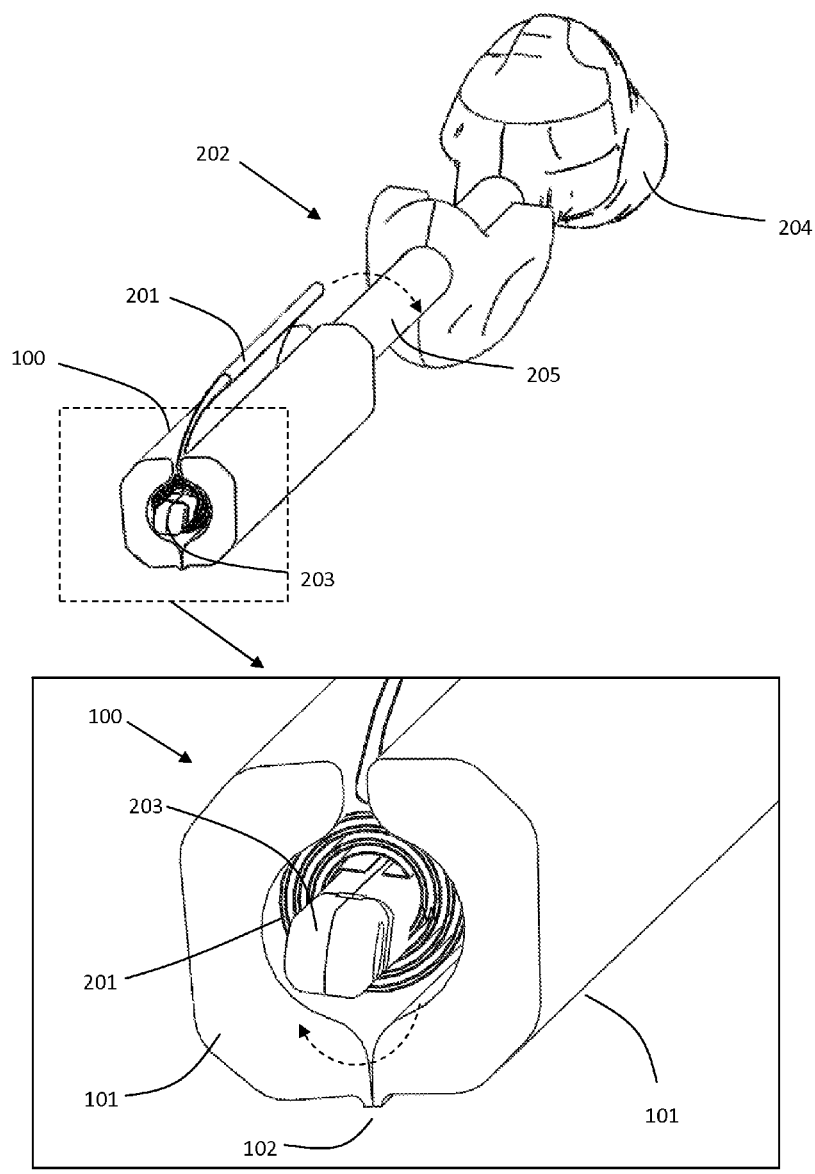
Figure 2D:
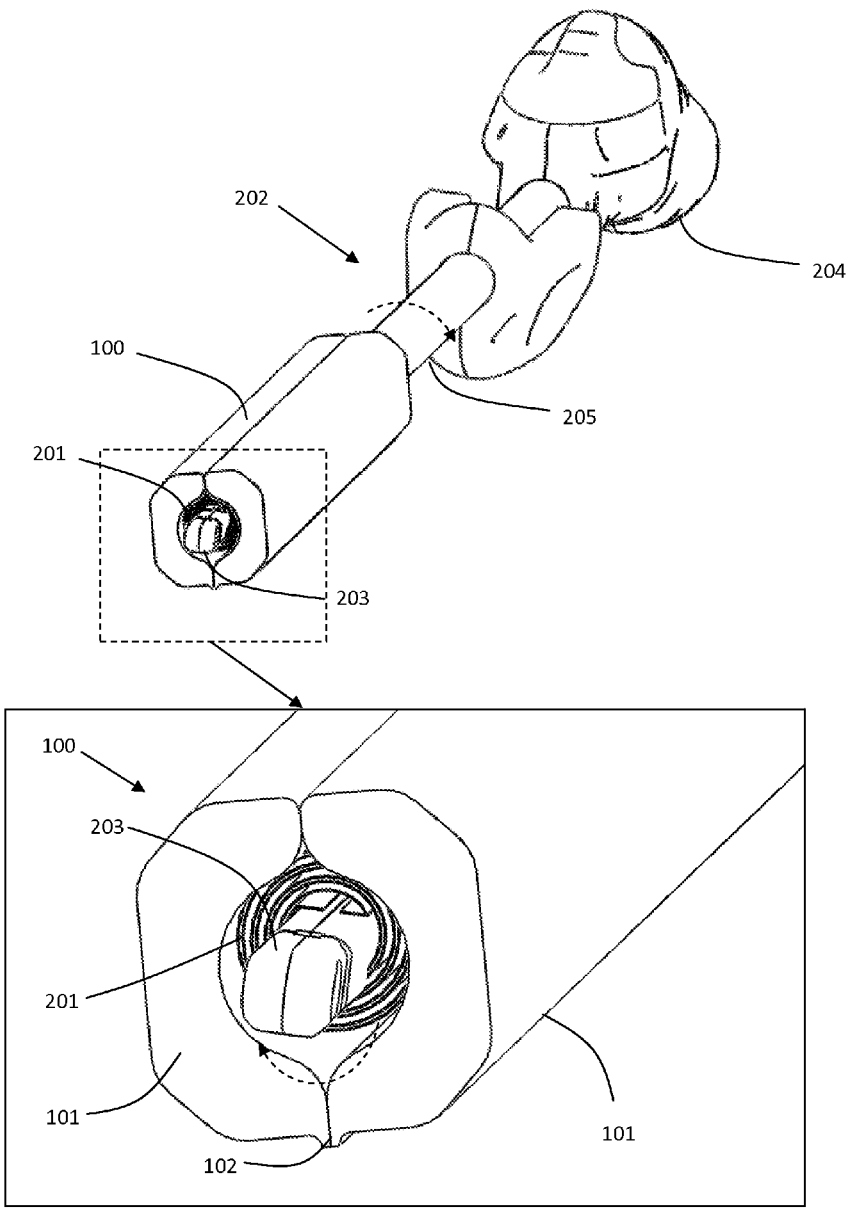
Figure 2E:
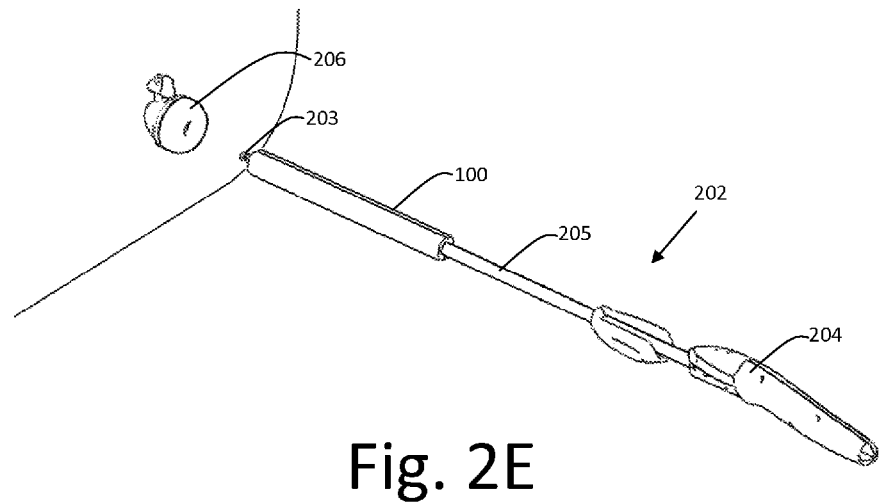
Figure 2F:
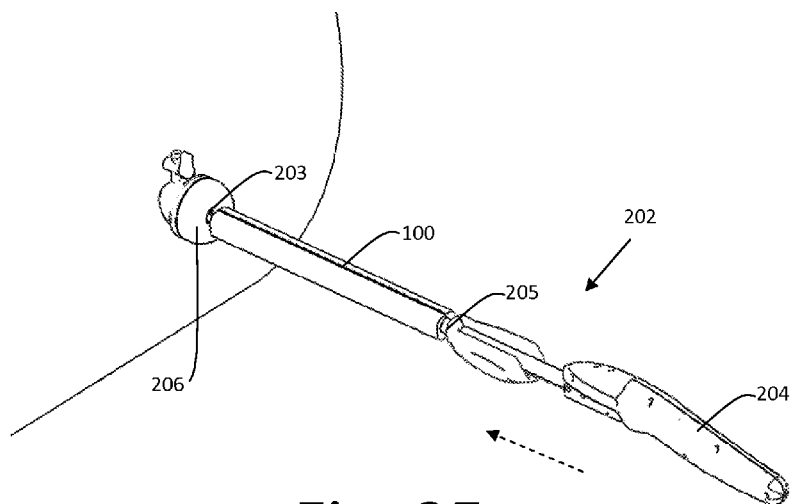
Figure 2G:
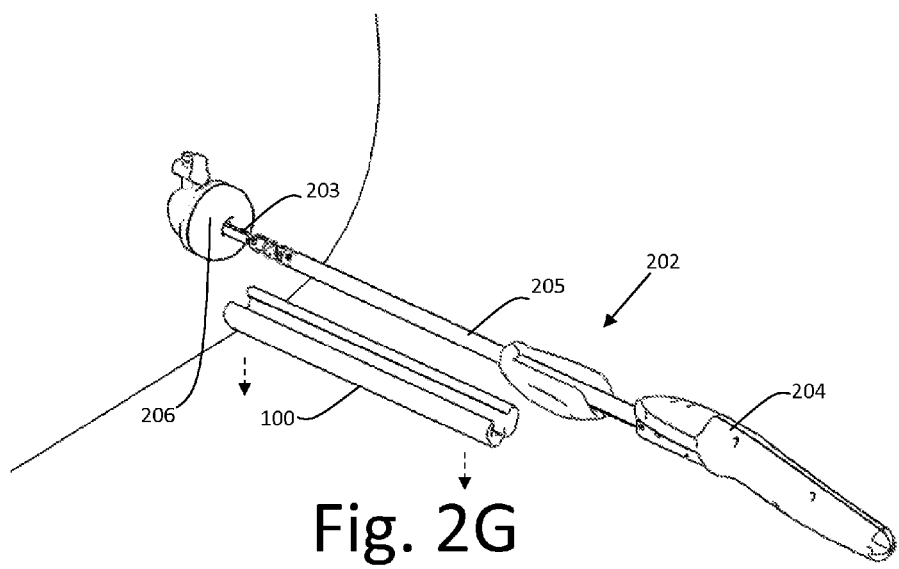

The method comprises steps selected inter alia from:
1. Obtaining a patch 201 and a PIS 202.
2. Attaching said patch 201 to said distal portion of said PIS 202 (FIG. 2A).
3. Obtaining PRA 100 in its said open configuration.
4. Inserting said distal portion 203 of said PIS 202 and at least a portion of said patch 201 into said PRA 100 through said gap W (FIG. 2B).
5. Rotating (rolling) said distal portion 203 and said patch 201 inside said PRA 100 while continually transforming said PRA from its said open configuration into its said closed configuration (FIG. 2C).
6. Continue rotating said distal portion 203 and said patch 201 inside said PRA 100 until the entire patch 201 in rolled inside PRA 100 (FIG. 2D).
7. Inserting said rolled patch 201 into a body cavity (e.g. abdominal cavity) through a laparoscopic cannula 206 or through an incision (FIG. 2E-2F).
8. Transforming said PRA 100 into its said open configuration and de-coupling it from said PIS 202 (FIG. 2G).

It should be mentioned that during said insertion of said patch into said body cavity, the distal portion can be subjected to large forces and therefore may be buckle or deformed.

in order to prevent such deformation, said PRA 100 additionally provides external support in order to prevent said buckling or deformation.

It also should be mentioned that said PRA 100 holds said patch 201 tightly rolled during said insertion to said body cavity. As a result said insertion is made with less resistance and therefore is faster and safer compare to manual insertion.

Figure 3A:
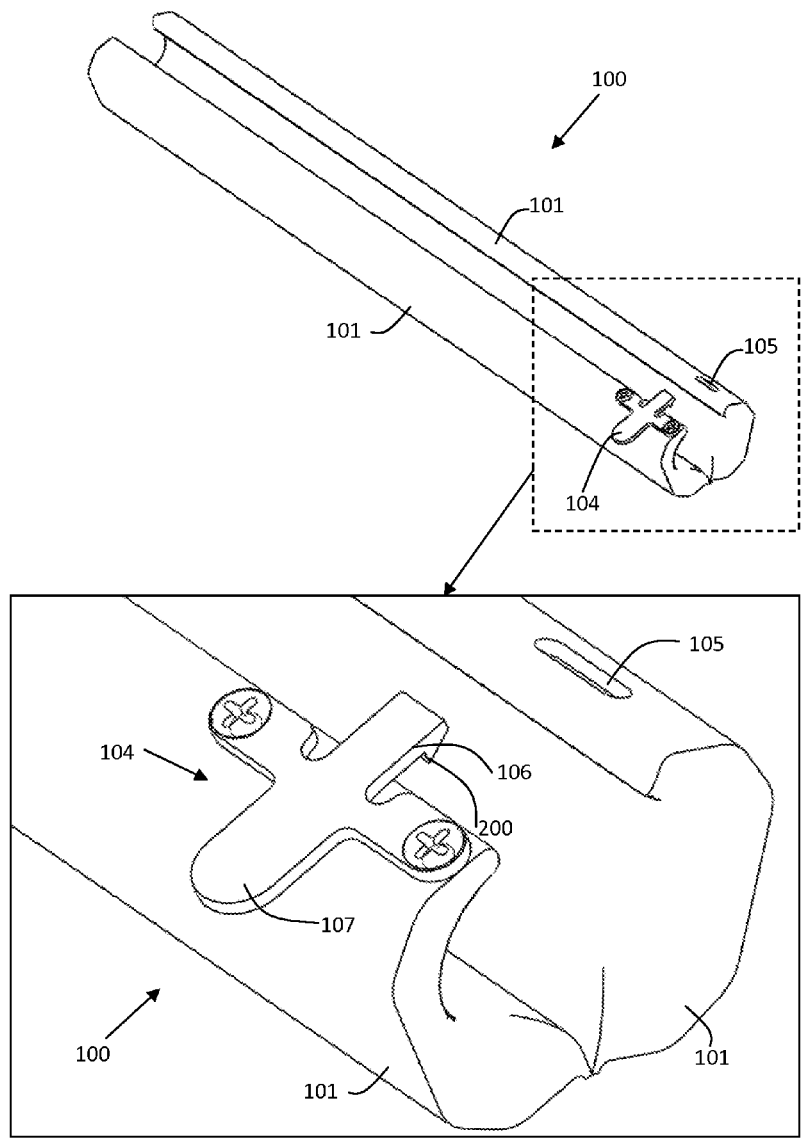
FIGS. 3A-3B illustrate another embodiment of the present invention in which a locking section (LS) is used.
Figure 3B:
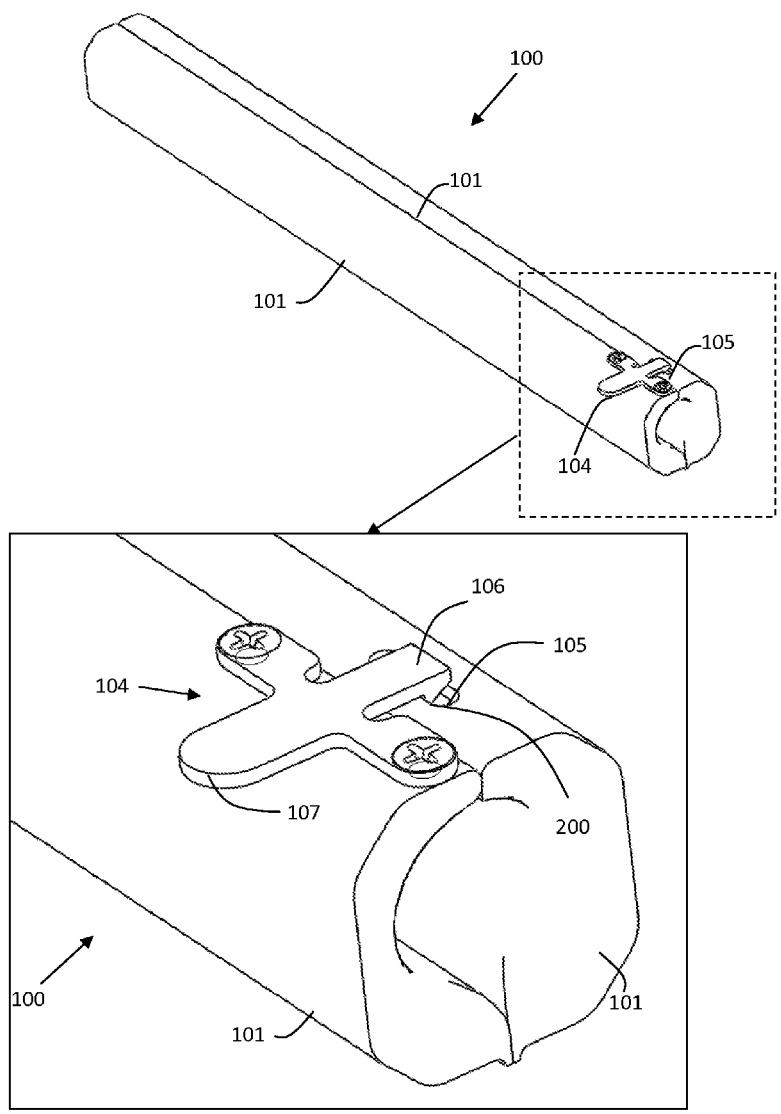
Figure 3C:
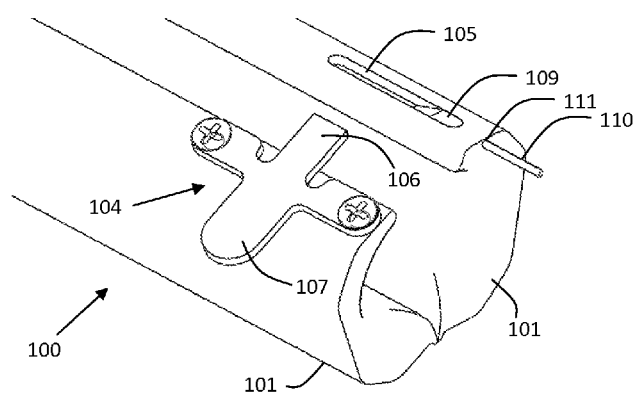
FIGS. 3C-3F illustrate another embodiment of the present invention in which an automatic release section (ARS) is used.

Reference is now being made to FIGS. 3A-3B which describe another embodiment of the present invention. According the this embodiment, said PRA 100 additionally comprises locking section (LS) 104 which is adapted to hold said PRA 100 in its said closed configuration.

Additionally said LS 104 allows the surgeon to release said locking when desired. According to this embodiment, said LS 104 comprises a locking hook 200, attached to one section 101 of said PRA 100 and a locking groove 105 located on the outer surface of the second section 101 of said PRA 100.

Said locking hook 200 comprises a locking tab 106, adapted to be hinged inside said groove 105 and a release tab 107, adapted to allow said release of said locking.

FIG. 3A describes said PRA 100 in its said open configuration; as can be seen from this figure, in the open configuration said locking tab 106 is not hinged inside said groove 105, therefore a free motion of said two sections 101 is enabled.

Once the said PRA 100 in transformed into its said close configuration, said locking tab 106 is inserted into said groove 105; and, therefore holding the two sections 101 together (see FIG. 3B). In order to reopen said PRA 100, the surgeon presses the release tab 107 of said LS 104 therefore elevating said hook tab out of said grove 105 and releasing the two sections 101 from one another.

Reference is now being made to FIGS. 3C-3F which illustrate another embodiment of the present invention. According to this embodiment, said LS 104 additionally comprises an automatic release section (ARS) which automatically releases the two sections 101 of said PRA 100 once said patch 201 is at least partially inserted into said body cavity.

Said ARS comprises a tab 109 and a pin 110. Said tab 109 has a tilted end and is initially located at the proximal end (relative to the surgeon) of said groove 105. Said pin 110 in located inside a hole 111 at section 101.

Figure 3D:
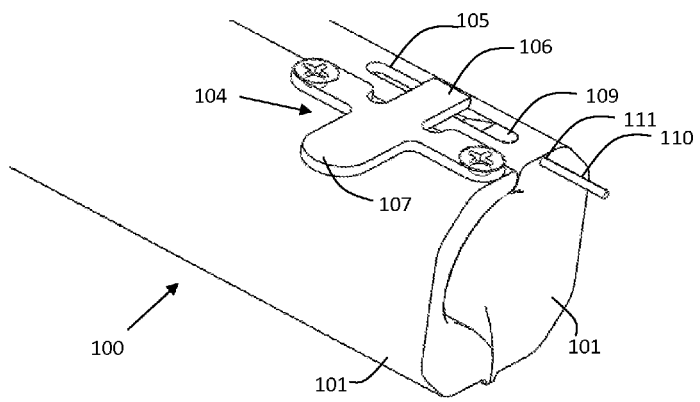

Once said PRA 100 is transformed into its said closed configuration said locking hook 110 is inserted into said groove 105 (see FIG. 3D).

Once said rolled patch is at least partially inserted into said body cavity, the proximal portion 204 of said PIS 202 pushes said pin 110 and said tab 109 toward the distal end of said groove 105.

Figure 3E:
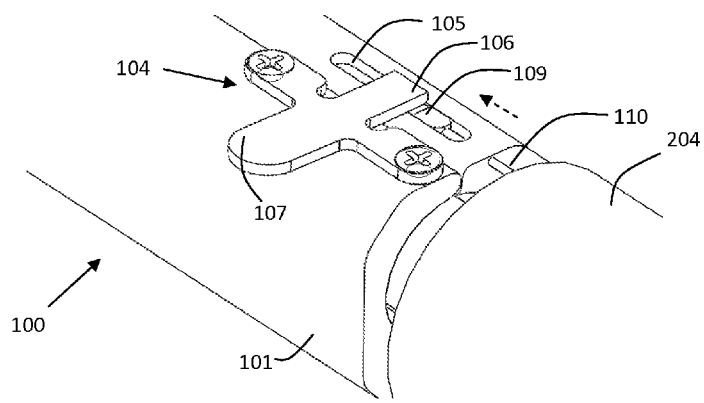
Figure 3F:
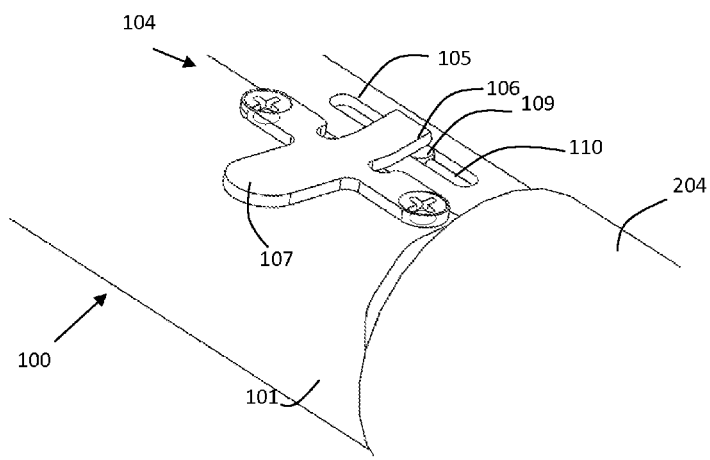

As a result tab 109 is pushing said locking tab 106 out of said grove and therefore releasing the two sections 101 (see FIGS. 3E and 3F).

Figure 4A:
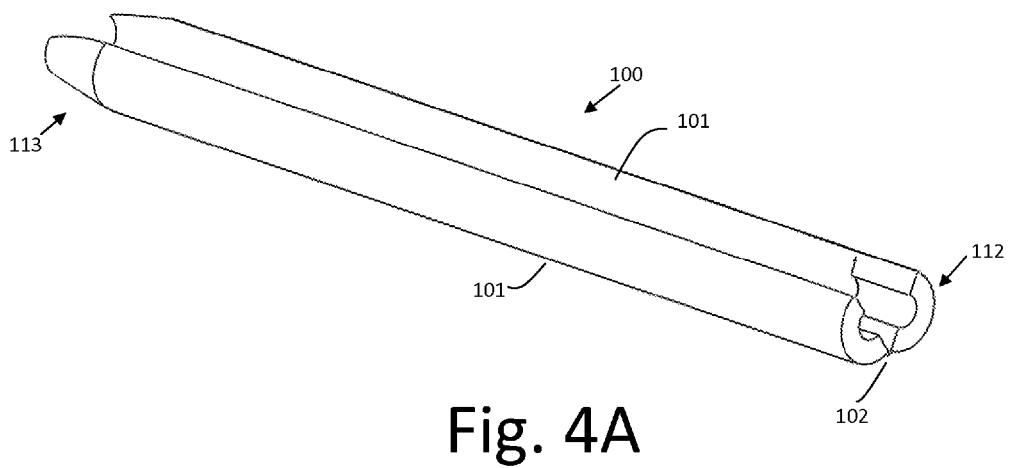
FIGS. 4A-4B illustrate another embodiment of the present invention in which an anti-buckling section ABS 112 and an insertion tip 113 is used.
Figure 4B:
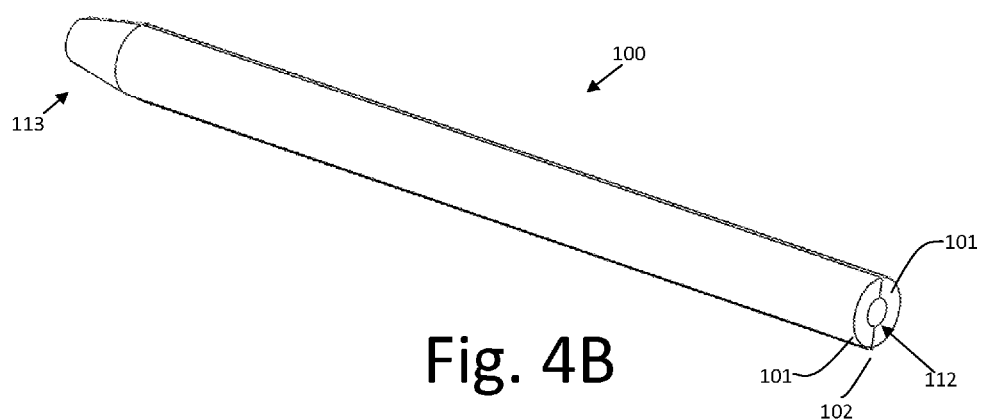

Reference is now being made to FIGS. 4A-4B which illustrate another embodiment of the present invention. According to this embodiment, said PRA 100 additionally comprises an anti-buckling section ABS 112 and an insertion tip 113.

Said ABS 112 is characterized by having a smaller inner diameter than the rest of said PRA 100. Said ABS 112 is adapted to tightly envelope the shaft of said PIS 202 such that lateral movement between said distal portion 203 of said PIS 202 and said shaft of said PIS is limited and therefore the risk that the distal portion of said PIS will buckle is reduced.

Said insertion tip 113 is characterized by having a conical shape and is adapted to assist inserting said rolled patch 201 into said body cavity through an incision. Once said patch is completely rolled inside said PRA the surgeon can at least partially insert said insertion tip 113 into said incision, therefore said rolled patch is substantially centered in relation to said incision during the initial stage of said insertion; in addition, said insertion tip 113 opens said incision and allowing an easier insertion of said patch into said body cavity through said incision.

Figure 4C:
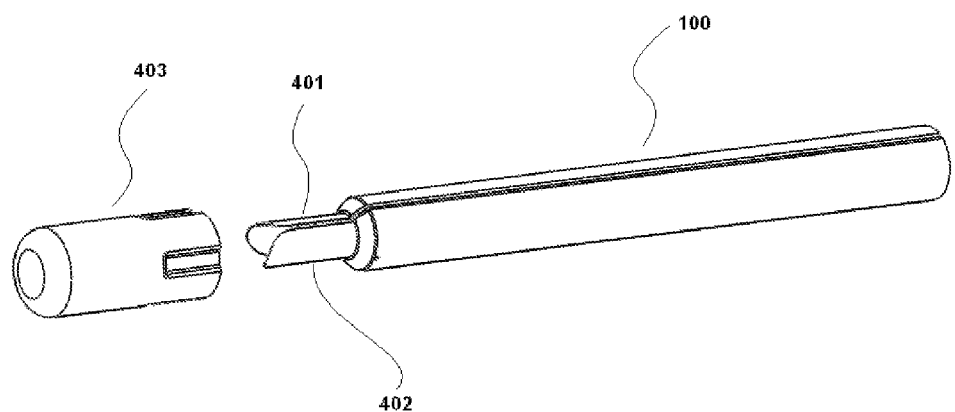
FIG. 4C is a perspective view of another embodiment of the present invention with a patch rolling apparatus having fins extending therefrom and a cap.

Reference is now made to FIG. 4C which illustrate another embodiment of the present invention. According to this embodiment, said PRA 100 additionally comprises insertion fins 401 and 402. These fins are adapted to allow a better insertion of a mesh through a port or an incision by opening the valve (in the case of a port) or the subcutaneous layer (in a case on an incision). This spreading is important since sometimes the port's valve or the tissue may drag the furled mesh backward along the shaft of the instrument during the insertion process, thus increasing its overall cross section and interfering with the insertion process. Spreading of the valve or the tissue reduces the overall friction, therefore allowing better insertion. The fins may be covered by a cap 403.

FIG. 5A-5E illustrate an embodiment of a furling clip (FC) 500. Said FC 500 is adapted to assist in rolling a prosthetic mesh around a surgical instrument (e.g. Grasper, mesh deployment device) by securing said patch to the shaft of said surgical instrument during said rolling. Said FC 500 is removed once such rolling is at least partially obtained.

Figure 5A:
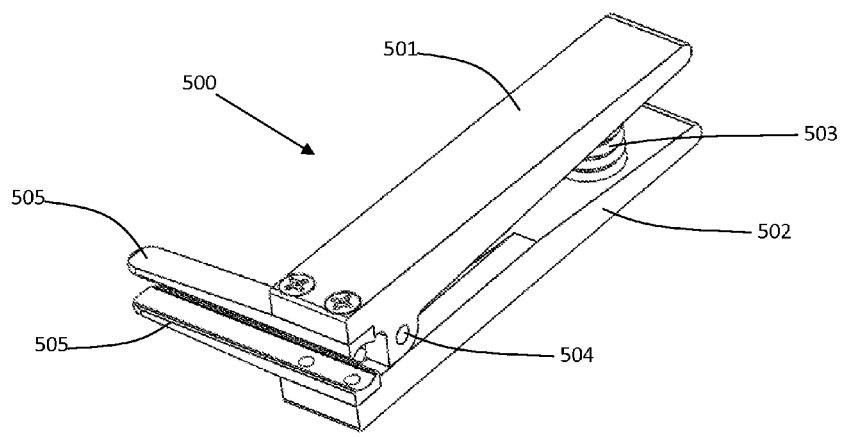
FIG. 5A is a persepctive view of an embodiment of a furling clip in a first configuration.
Figure 5B:
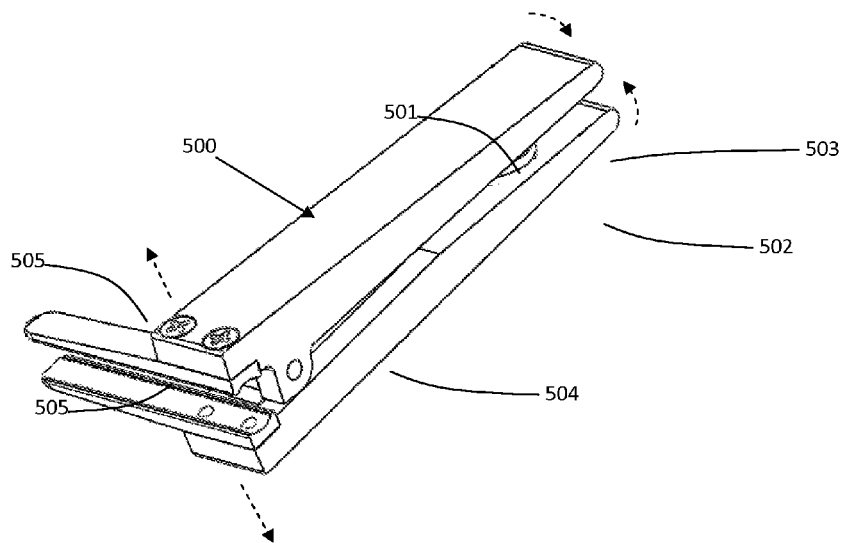
FIG. 5B is a perspective view of the furling clip of FIG. 5A in a second configuration.

In a preferred embodiment, described in FIG. 5A-5B, said FC 500 comprises two sections 501 and 502 which are connected via a hinge 504. A spring 503 is placed between sections 501 and 502 in order to provide clamping force. A clamping edge 505 is located at the distal end of each section 501 and 502, said clamping edge 505 is adapted to hold said mesh and said shaft of said instrument, while allowing the mesh to be rolled only around them and not around the sections 501 & 502; therefore allowing better rolling of the mesh around the shaft and enabling the removal of said FC 500 from said shaft once said rolling is accomplished. Once the proximal end of each section 501 and 502 is squeezed, the two clamping edges are distanced from one another, hence, allowing to locate said FC 500 on said shaft (FIG. 5B). once the pressure is removed spring 503 clamp said FC 500 on said mesh and shaft.

Figure 5C:
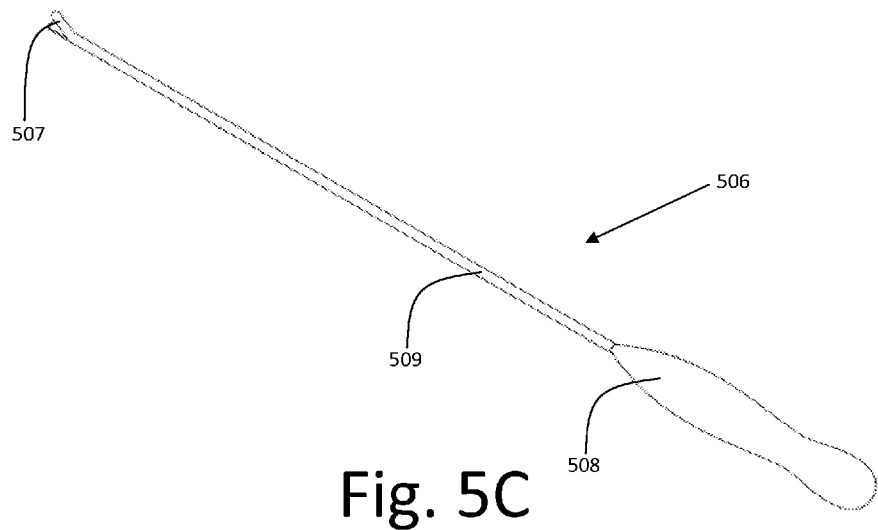
FIGS. 5C-5E illustrate a method of using the furling clip of FIG. 5A during rolling of a mesh onto a surgical instrument.
Figure 5D:
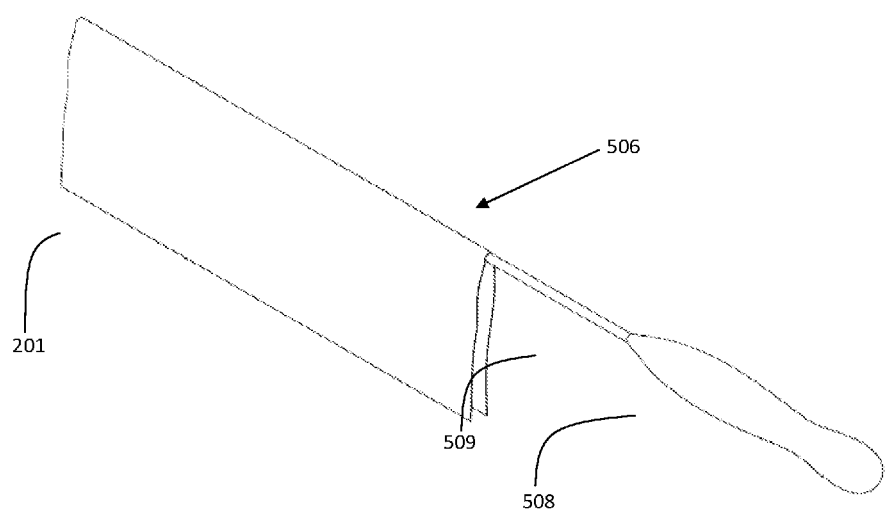
Figure 5E:
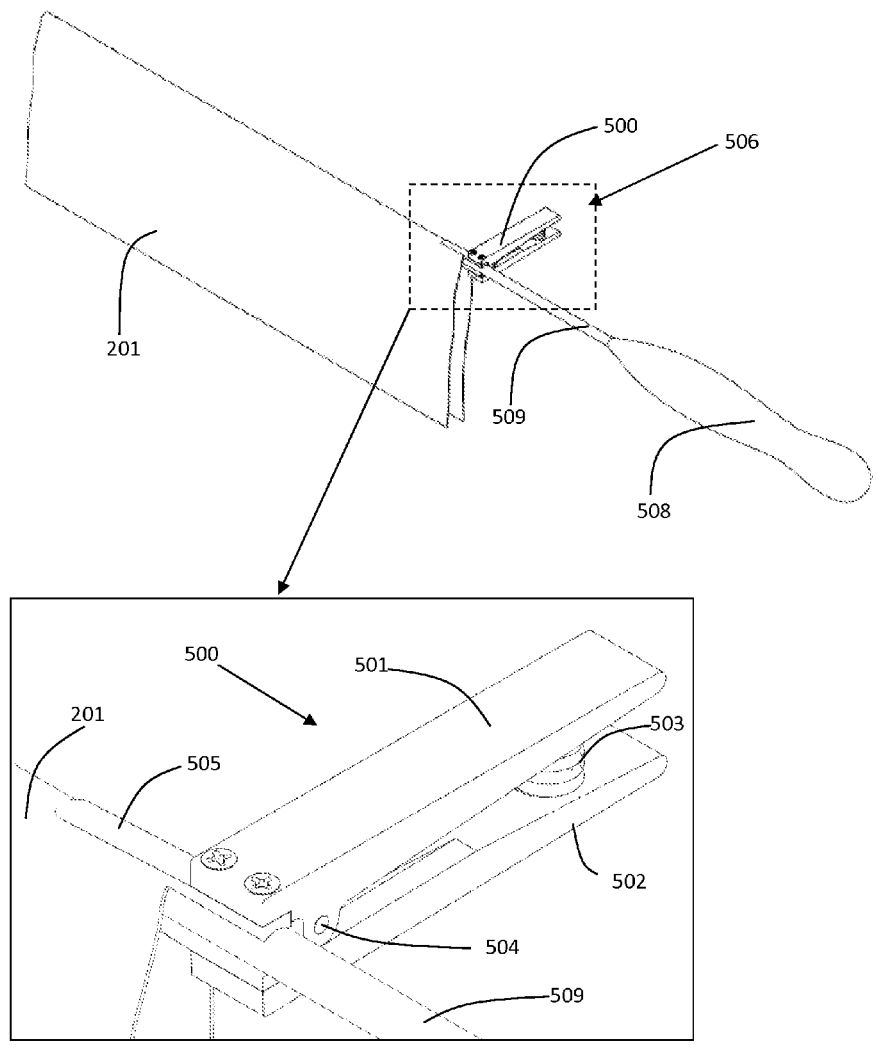

FIGS. 5C-5E describes a method of using FC 500 during rolling of a mesh 201 on a surgical instrument 509. In this case the instrument is a standard grasper which comprises a handle 508, a shaft 509 and a forceps 507 (FIG. 5C). During the operation, the surgeon places a mesh 201 on top of the shaft 509 and secures it by forceps 507 (FIG. 5D). In order to prevent slipping of the rear portion of the mesh, and in order to facilitate tight and ever rolling of the mesh 201 around the shaft 509, the surgeon places a FC 500 at the proximal edge of the mesh 201 (FIG. 5E). Said clamping edges 505 of said edge are protrude beyond the edge of each section 501 and 502, enabling the surgeon to roll the mesh around them. The rolling can be made either manually or by a patch rolling apparatus. Once said patch 201 is substantially rolled, said FC 500 is removed from the shaft 509 by squishing sections 501 & 502 and pulling FC 500 back, then the mesh 201 is inserted to the abdominal cavity.

Incorporation By Reference

References and citations to other documents, such as patents, patent applications, patent publications, journals, books, papers, web contents, have been made throughout this disclosure. All such documents are hereby incorporated herein by reference in their entirety for all purposes.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A device for facilitating rolling of a surgical mesh onto a surgical instrument, the device comprising:
    a sleeve having a slit along a length of the sleeve, wherein the sleeve comprises portions movable to an open configuration for operably coupling with an unrolled mesh on a surgical instrument, and a closed configuration for facilitating rolling of the mesh onto the instrument; and
    a plurality of rigid members connected to a distal end of the sleeve, the rigid members are adapted to open valves of surgical ports.

2. The device according to claim 1, portions of the sleeve comprises:
    a first portion; and
    a second portion, wherein the first and second portion are hingedly connected.

3. The device according to claim 1, further comprising a locking mechanism for locking the sleeve when it is in the closed configuration.

4. The device according to claim 3, wherein the locking mechanism further comprises a member that provides for automatic release of the locked sleeve once the mesh is at least partially inserted into a body cavity.

5. The device according to claim 1, further comprising an insertion tip.

6. The device of claim 1, wherein the rigid members are fins.

7. The device according to claim 1, wherein the fins are adapted to cause spreading of a subcutaneous layer of tissue.

8. The device according to claim 1, wherein the mesh is a patch.

9. The device according to claim 8, wherein the instrument is a patch deployment apparatus or a laparoscopic grasper.

10. The device according to claim 1, further comprising a member at a distal portion of the sleeve that prevents bucking of a shaft of a patch deployment apparatus or a laparoscopic grasper.

11. A method for facilitating rolling of a mesh onto a surgical instrument, the method comprising:
    operably coupling a device that facilitates rolling of an unrolled mesh on a surgical instrument, wherein the device comprises a sleeve having a slit along a length of the sleeve, wherein the sleeve has an open configuration for operably coupling with an unrolled mesh on a surgical instrument, and a closed configuration for facilitating rolling of the mesh onto the instrument, wherein the sleeve further comprises a plurality of rigid members connected to a distal end of the sleeve;
    using the device to thereby roll the mesh on the instrument; and
    advancing the instrument such that the rigid members of the sleeve spread apart subcutaneous tissue, thereby allowing advancement of the instrument having the rolled mesh into a patient.

12. The method according to claim 11, further comprising prior to the coupling step, placing the unrolled mesh onto the surgical instrument.

13. The method according to claim 12, further comprising prior to the coupling step, attaching the unrolled mesh to the instrument via a clip.

14. The method according to claim 11, wherein the mesh is a patch.

15. The method according to claim 14, wherein the instrument is a patch deployment apparatus.

16. A method for facilitating rolling of a mesh onto a surgical instrument, the method comprising:
   operably coupling a device that facilitates rolling of an unrolled mesh on a surgical instrument, wherein the device comprises a sleeve having a slit along a length of the sleeve, wherein the sleeve has an open configuration for operably coupling with an unrolled mesh on a surgical instrument, and a closed configuration for facilitating rolling of the mesh onto the instrument, wherein the sleeve further comprises a plurality of rigid members connected to a distal end of the sleeve;
   using the device to thereby roll the mesh on the instrument; and
   advancing the instrument such that the rigid members of the sleeve open a closed of a surgical port, thereby allowing advancement of the instrument having the rolled mesh into a patient.

* * * * *